United States Patent
Kawaguchi et al.

(10) Patent No.: US 9,777,103 B2
(45) Date of Patent: Oct. 3, 2017

(54) POLYTHIOL COMPOSITION, POLYMERIZABLE COMPOSITION FOR OPTICAL MATERIAL AND USE THEREOF

(71) Applicant: MITSUI CHEMICALS, INC., Minato-ku (JP)

(72) Inventors: Masaru Kawaguchi, Omuta (JP); Takeshi Nishimura, Yanagawa (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/395,146

(22) PCT Filed: Aug. 13, 2013

(86) PCT No.: PCT/JP2013/071891
§ 371 (c)(1),
(2) Date: Oct. 17, 2014

(87) PCT Pub. No.: WO2014/027665
PCT Pub. Date: Feb. 20, 2014

(65) Prior Publication Data
US 2015/0094443 A1 Apr. 2, 2015

(30) Foreign Application Priority Data

Aug. 14, 2012 (JP) .................................. 2012-179899
Feb. 28, 2013 (WO) ................... PCT/JP2013/001201

(51) Int. Cl.
*C08G 18/38* (2006.01)
*C07C 321/14* (2006.01)
*C08G 18/76* (2006.01)
*G02B 1/04* (2006.01)

(52) U.S. Cl.
CPC ........ *C08G 18/3876* (2013.01); *C07C 321/14* (2013.01); *C08G 18/7642* (2013.01); *G02B 1/041* (2013.01)

(58) Field of Classification Search
CPC ....................... C08G 18/3876; C08G 18/7642; G02B 1/041; C07C 321/14; C08L 175/04; C08L 181/00; C08L 75/04; C08L 81/00
See application file for complete search history.

(56) References Cited

U.S. PATENT DOCUMENTS 5,087,758 A 2/1992 Kanemura et al.
5,352,758 A 10/1994 Kanemura et al.
(Continued)

FOREIGN PATENT DOCUMENTS

JP 2-270859 A 11/1990
JP 5-208950 A 8/1993
(Continued)

OTHER PUBLICATIONS

International Search Report (PCT/ISA/210) mailed on Sep. 24, 2013, by the Japanese Patent Office as the International Searching Authority for International Application No. PCT/JP2013/071891.
(Continued)

*Primary Examiner* — Michael L Leonard
(74) *Attorney, Agent, or Firm* — Buchanan, Ingersoll & Rooney PC

(57) ABSTRACT

A polythiol composition according to the present invention includes a polythiol compound (A) having three or more mercapto groups and a nitrogen-containing compound (B) in which one of a mercapto group of the polythiol compound (A) is replaced with a group represented by the following formula (a) and other one of a mercapto group of the polythiol compound (A) is replaced with a hydroxyl group, in which the peak area of the nitrogen-containing compound (B) is equal to or less than 3.0 with respect to the peak area of 100 of the polythiol compound (A) in a high performance liquid chromatography measurement.

(Continued)

(a)

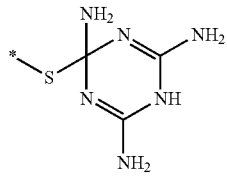

FOREIGN PATENT DOCUMENTS

| JP | 7-252207 A | 10/1995 |
|---|---|---|
| JP | 9-052931 A | 2/1997 |
| JP | 9-194558 A | 7/1997 |
| JP | 9-263575 A | 10/1997 |
| JP | 9-286772 A | 11/1997 |
| JP | 10-095827 A | 4/1998 |
| JP | 2001-039944 A | 2/2001 |
| WO | WO 2007/129449 A1 | 11/2007 |
| WO | WO 2007/129450 A1 | 11/2007 |

8 Claims, 2 Drawing Sheets

(56) References Cited

U.S. PATENT DOCUMENTS

| 5,608,115 A | 3/1997 | Okazaki et al. |
| 2009/0264613 A1 | 10/2009 | Kuma et al. |

OTHER PUBLICATIONS

Written Opinion (PCT/ISA/237) mailed on Sep. 24, 2013, by the Japanese Patent Office as the International Searching Authority for International Application No. PCT/JP2013/071891.

International Preliminary Report on Patentability (PCT/IPEA/409) mailed on Aug. 14, 2012 for International Application No. PCT/JP2013/071891 (with partial English language translation).

POLYTHIOL COMPOSITION, POLYMERIZABLE COMPOSITION FOR OPTICAL MATERIAL AND USE THEREOF

TECHNICAL FIELD

The present invention relates to a polythiol composition, a polymerizable composition for an optical material and use thereof.

BACKGROUND ART

Since a plastic lens is lighter, hardly broken and capable of being dyed, compared to an inorganic lens, the plastic lens has recently become widely used rapidly in an optical element such as a spectacle lens or a camera lens.

Higher performance has been demanded for a resin for the plastic lens and high refractive index, high Abbe number, low density, high heat-resistance, or the like has been required. So far various kinds of resin materials for the lens have been developed and used.

Among these, an optical material comprised of a polythiourethane-based resin has high refractive index and high Abbe number, and is excellent in the impact resistance, the dyeability, the processability, or the like. The polythiourethane-based resin can be obtained by reacting a polythiol with a polyiso(thio)cyanate compound, or the like.

In a case of using in the plastic lens, the polythiourethane-based resin is required to cause less coloration, have excellent resin color and be transparence. In a case where the quality of polythiol was deteriorated, there were cases where the quality of the obtained resin was also deteriorated.

Patent documents which relate to a process of producing polythiol include the following patent documents.

In Patent Document 1 or Patent Document 2, a method in which 2-mercaptoethanol reacts with epichlorohydrin, the obtained compound reacts with thiourea to obtain an isothiuronium salt, and next the isothiuronium salt is hydrolyzed to obtain the specific polythiol compound is described.

In Patent Document 3, a process of producing a polythiol compound in which the amount of the specific impurities included in 2-mercaptoethanol is set to the predetermined range is described.

In Patent Document 4, a process of producing a polythiol compound in which calcium content included in thiourea is set to the predetermined range is described.

RELATED DOCUMENT

Patent Document

[Patent Document 1] Japanese Unexamined Patent Publication No. 2-270859
[Patent Document 2] Japanese Unexamined Patent Publication No. 7-252207
[Patent Document 3] PCT International Publication No. 2007/129449
[Patent Document 4] PCT International Publication No. 2007/129450

DISCLOSURE OF THE INVENTION

However, in a case where the plastic lens comprised of the polythiourethane-based resin is produced by using the polythiol compound obtained in the methods described in the documents, there was room for improvement of optical properties such as color, transparency, striation.

The present inventors ascertained that a trace of the specific component is included in the polythiol compound, as a result of extensive studies in order to improve the optical properties, and found that the specific component included at the predetermined amount affects the reaction (polymerization) activity in a reaction (polymerization reaction) of the polythiol compound and a polyisocyanate compound.

The present invention can be given as below.

[1] A polythiol composition includes a polythiol compound (A) having three or more mercapto groups, and a nitrogen-containing compound (B) in which at least one of a mercapto group of the polythiol compound (A) is replaced with a group represented by the following formula (a)

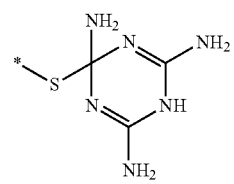

wherein, in the formula, * represents an atomic bonding, and at least other one of a mercapto group of the polythiol compound (A) is replaced with a hydroxyl group, in which the peak area of the nitrogen-containing compound (B) is equal to or less than 3.0, with respect to the peak area of 100 of the polythiol compound (A) in a high performance liquid chromatography measurement.

[2] The polythiol composition according to [1], in which the polythiol compound (A) is represented by the following formula (5).

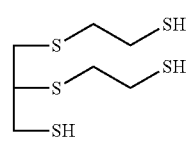

[3] The polythiol composition according to [1], in which the polythiol compound (A) is primarily comprised of at least one kind selected from the compounds represented by the following formulae (6) to (8).

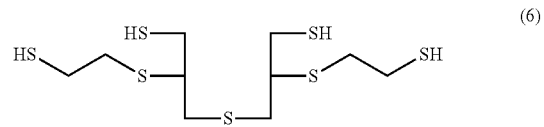

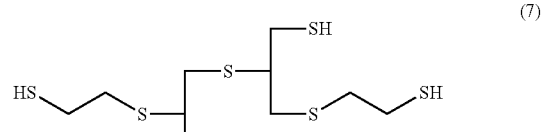

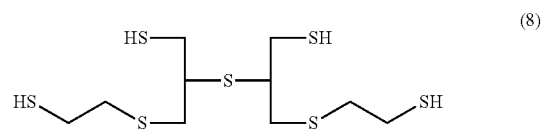

[4] A polymerizable composition for an optical material includes the polythiol composition according to any of [1] to [3] and a poly(thio)isocyanate compound.

[5] A method of manufacturing a molded product, comprising mixing the polythiol composition according to any of [1] to [3] and a poly(thio)isocyanate compound to obtain a polymerizable composition for an optical material; and puting the polymerizable composition into a mold and curing the composition.

[6] A molded product which is obtained by curing the polymerizable composition according to [4].

[7] An optical element comprised of the molded product according to [6].

[8] A lens which comprised of the optical element according to [7].

It is possible to obtain a plastic lens comprised of the polythiourethane-based resin which is excellent in quality such as color, transparency, striation by using the polythiol composition of the present invention.

That is, according to the present invention, by setting the nitrogen-containing compound (B) which is a trace component included in the polythiol composition to within the predetermined range, a plastic lens product in which the high quality such as color, transparency, striation, or the like is demanded can be industrially produced with a satisfactory yield. Furthermore, when the polymerizable composition is prepared, by adjusting the amount of the nitrogen-containing compound (B) included in the polythiol composition and further confirming the amount, it is possible to suppress the occurrence of defects in quality such as striation or coloration of the plastic lens, and thus it is possible to improve the yield of product.

DESCRIPTION OF EMBODIMENTS

Figure 1:
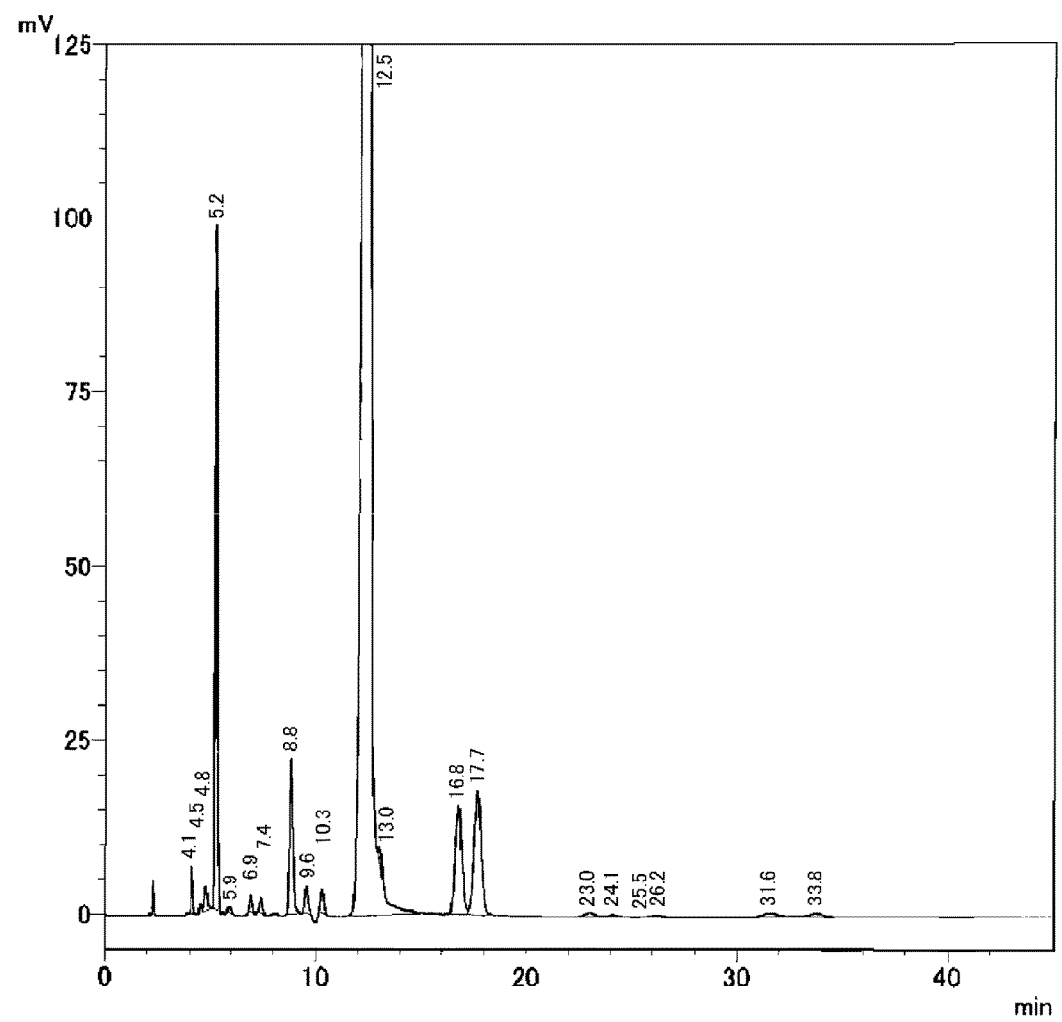
FIG. 1 shows an HPLC chart of a polythiol composition obtained in Example A-1.

Hereinafter, description will be given of a polythiol composition of the present invention based on embodiments.

The polythiol composition of the present embodiment includes a polythiol compound (A) and a nitrogen-containing compound (B). Hereinafter, description will be given of each component.

(Polythiol Compound (A))

The polythiol compound (A) is a polythiol compound having three or more mercapto groups.

A polythiol compound (A) includes an aliphatic polythiol compound such as 1,2,3-propanetrithiol, tetrakis(mercaptomethyl)methane, trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, ester of these polythiols and the thioglycolic acids or mercaptopropionic acid, 1,1,3,3-tetrakis(mercaptomethylthio) propane, 1,1,2,2-tetrakis(mercaptomethylthio)ethane, 4,6-bis(mercaptomethylthio)-1,3-dithiacyclohexane, tris(mercaptomethylthio)methane, and tris(mercaptoethylthio) methane; an aromatic polythiol compound such as 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene.

However, the polythiol compound (A) is not limited to only the exemplary compounds.

In the present embodiment, as a polythiol compound (A), a polythiol compound which is primarily comprised of at least one kind selected from the group consisting of 4-mercaptomethyl-1,8-dimercapto-3,6-dithiaoctane represented by the following formula (5), 4,8-dimercaptomethyl-1,11-dimercapto-3,6,9-trithiaundecane represented by the following formula (6), 4,7-dimercaptomethyl-1,11-dimercapto-3,6,9-trithiaundecane represented by the following formula (7), and 5,7-dimercaptomethyl-1,11-dimercapto-3,6,9-trithiaundecane represented by the following formula (8) can be preferably used.

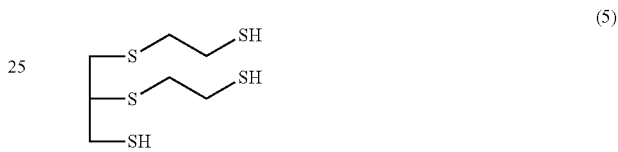

(5)

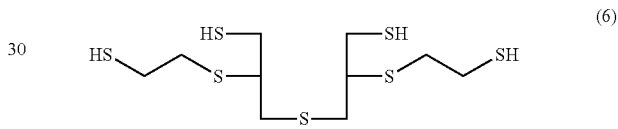

(6)

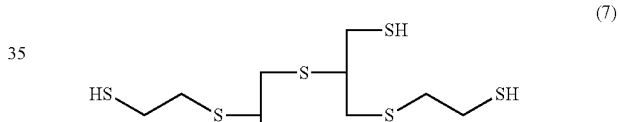

(7)

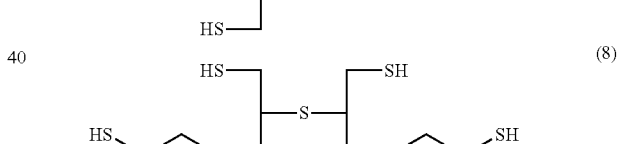

(8)

(Nitrogen-Containing Compound (B))

The nitrogen-containing compound (B) has a structure in which at least one of a mercapto group of the polythiol compound (A) having three or more mercapto groups is replaced with a group represented by the following formula (a) and at least one other mercapto group of the polythiol compound (A) is replaced with a hydroxyl group.

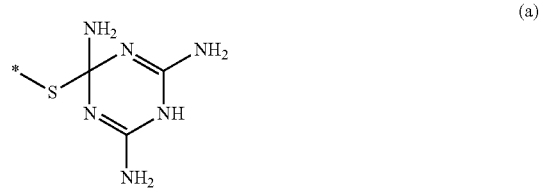 [SMILES: *SC1(N)N=C(N)NC(N)=N1]

(a)

In the formula, * represents an atomic bonding.

Moreover, the nitrogen-containing compound (B) can include a salt of the compound having the structure described above. The salt is not particularly limited, however, for example, includes carboxylic acid such as acetic acid, an organic acid such as methanesulfonic acid, a compound having a mercapto (SH) group, an inorganic acid such as hydrochloric acid, sulfuric acid or phosphoric acid.

In the polythiol composition of the present embodiment, the peak area of the nitrogen-containing compound (B) to the peak area of 100 of the polythiol compound (A) (hereinafter, also referred to simply as "the ratio of the peak area of the nitrogen-containing compound (B)") is equal to or less than 3.0, preferably equal to or less than 1.5, and more preferably equal to or less than 0.50 in a high performance liquid chromatography measurement. The lower limit of the ratio of the peak area of the nitrogen-containing compound (B) does not particularly exist, however, is preferably equal to or more than 0.01, considering the number of step in purification in an industrial production scale.

In the usual case, the nitrogen-containing compound (B) is a mixture of a plurality of isomers, and appears as a peak at the predetermined retention time in high performance liquid chromatography. Moreover, the peaks of the nitrogen-containing compound (B) which is a mixture of a plurality of isomers may be overlapped.

By setting the ratio of the peak area of the nitrogen-containing compound (B) to the range described above, it is possible to obtain the plastic lens comprised of the polythiourethane-based resin which is excellent in quality such as color, transparency, striation.

The ratio of the peak area of the nitrogen-containing compound (B) can be calculated from the following expression based on the peak area of high performance liquid chromatography.

{[peak area of nitrogen-containing compound (B)]/ [peak area of polythiol compound (A)]}×100    Expression Moreover, the conditions of high performance liquid chromatography are appropriately selected according to structures, properties, or the like of the polythiol compound (A) and the nitrogen-containing compound (B).

The ratio of the peak area of the nitrogen-containing compound (B) in the present embodiment, for example, can be described, in a case where the polythiol compound (A) is "4-mercaptomethyl-1,8-dimercapto-3,6-dithiaoctane" and the nitrogen-containing compound (B) is "a compound in which one of a mercapto group of the polythiol compound (A) is replaced with a group represented by the formula (a) described above and other one of a mercapto group is replaced with a hydroxyl group.

In a case of measuring by high performance liquid chromatography under the conditions described below and calculating the ratio of the peak area of the nitrogen-containing compound (B) based on the expression described above, the peak area of the nitrogen-containing compound (B) which appears at the retention time from 4.3 minutes to 5.6 minutes is equal to or less than 3.0, preferably equal to or less than 1.0, and more preferably equal to or less than 0.50, with respect to the peak area of 100 of the polythiol compound (A) which appears at the retention time from 12.0 minutes to 13.5 minutes. The lower limit of the ratio of the peak area of the nitrogen-containing compound (B) does not particularly exist, however, is preferably equal to or more than 0.01, considering the number of step in purification in an industrial production scale.

Moreover, in a case of measuring under the conditions described below, any peak of the nitrogen-containing compound (B) which is a mixture of a plurality of isomers appears within the retention time described above and each peak may be overlapped.

Measurement conditions of high performance liquid chromatography
Column: YMC-Pack ODS-A A-312 (S5Φ6 mm×150 mm)
Mobile phase: acetonitrile/0.01 mol-potassium dihydrogen phosphate aqueous solution=60/40 (vol/vol)
Column temperature: 40° C.
Flow rate: 1.0 ml/min
Detector: UV detector, wavelength 230 nm
Preparation of measurement solution: 160 mg of a sample is dissolved and mixed in 10 ml of acetonitrile.
Injection volume: 2 µL Furthermore, the ratio of the peak area of the nitrogen-containing compound (B) in the present embodiment, for example, can also be described in a case where the polythiol compound (A) is "a polythiol compound which is primarily comprised of at least one kind selected from the group consisting of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane" and the nitrogen-containing compound (B) is "a compound in which one of a mercapto group of the polythiol compound (A) is replaced with a group represented by the formula (a) described above and other one of mercapto group is replaced with a hydroxyl group".

In a case of measuring by high performance liquid chromatography under the conditions described below and calculating the ratio of the peak area of the nitrogen-containing compound (B) based on the expression described above, the peak area of the nitrogen-containing compound (B) which appears at the retention time from 6.5 minutes to 8.0 minutes is equal to or less than 3.0, preferably equal to or less than 2.0, and more preferably equal to or less than 1.5, with respect to the peak area of 100 of the polythiol compound (A) which appears at the retention time from 22.0 minutes to 28.0 minutes. The lower limit of the ratio of the peak area of the nitrogen-containing compound (B) does not particularly exist, however, is preferably equal to or more than 0.01, considering the number of step in purification in an industrial production scale.

Moreover, in a case of measuring under the conditions described below, any peak of the nitrogen-containing compound (B) which is a mixture of a plurality of isomers appears within the retention time described above and each peak may be overlapped.

Measurement conditions of high performance liquid chromatography
Column: YMC-Pack ODS-A A-312 (S5Φ6 mm×150 mm)
Mobile phase: acetonitrile/0.01 mol-potassium dihydrogen phosphate aqueous solution=60/40 (vol/vol)
Column temperature: 40° C.
Flow rate: 1.0 ml/min
Detector: UV detector, wavelength 230 nm
Preparation of measurement solution: 160 mg of a sample is dissolved and mixed in 10 ml of acetonitrile.
Injection volume: 2 µL By setting the ratio of the peak area of the nitrogen-containing compound (B) to the range described above, it is possible to obtain the plastic lens comprised of the polythiourethane-based resin which is excellent in quality such as color, transparency and striation.

As described above, in the present embodiment, by giving two types of the polythiol compound described above as a polythiol compound (A), as an example, a case where the nitrogen-containing compound (B) is "a compound in which one of a mercapto group of two types of the polythiol compound described above is replaced with a group represented by the formula (a) described above and other one of a mercapto group is replaced with a hydroxyl group" has been described, however, aspects including the nitrogen-containing compound (B) as (1) or (2) described below may also be included.

(1) The nitrogen-containing compound (B) in which at least one of a mercapto group of two types of the polythiol compound described above is replaced with a group represented by the formula (a) described above and at least two mercapto groups are replaced with a hydroxyl group.

(2) The nitrogen-containing compound (B) in which at least two of a mercapto group of two types of the polythiol compound described above are replaced with a group represented by the formula (a) described above and at least one of a mercapto group is replaced with a hydroxyl group.

In addition, in the present embodiment, a case where the polythiol compound (A) are two types of the polythiol compound described above is given as an example to be described, however, a polythiol compound except these two types selected from the exemplified polythiol compound describe above can also be used.

<Process for Producing Polythiol Composition>

The polythiol composition of the present embodiment can be produced by the following steps.

Step A: The polyalcohol compound is obtained.

Step B: The polyalcohol compound obtained in the step A reacts with thiourea in the presence of hydrogen chloride to obtain an isothiuronium salt.

Step C: while a reaction solution including the isothiuronium salt obtained in the step B is maintained at the temperature from 20° C. to 60° C., aqueous ammonia is added into the reaction solution within 80 minutes and the isothiuronium salt is hydrolyzed at the temperature from 20° C. to 60° C. to obtain the polythiol composition.

Step D: The polythiol composition obtained in the step C is purified.

In the present embodiment, the cases where the polythiol compositions including two types of the polythiol compound described below are obtained are described.

As a polythiol compound, a case of producing "a polythiol compound which is primarily comprised of 4-mercaptomethyl-1,8-dimercapto-3,6-dithiaoctan" is set to an embodiment I and a case of producing "a polythiol compound which is primarily comprised of at least one kind selected from the group consisting of 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane" is set to an embodiment II to be described.

[Embodiment I]

Hereinafter, each step will be described in order.

(Step A)

In the step A, a 2-mercaptoethanol reacts with an epihalohydrin compound represented by the following formula (1), thereby it is possible to obtain a triol compound represented by the following formula (2) as a polyalcohol compound.

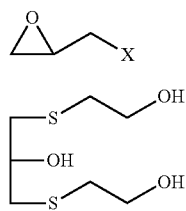

In the formula (1), X is a halogen atom which is a fluorine atom, a chlorine atom, a bromine atom, or an iodine atom, and preferably a chlorine atom.

In the present embodiment, the reaction can be performed in a range from 10° C. to 50° C., preferably from 15° C. to 50° C., and more preferably from 25° C. to 45° C. The reaction temperature is lower than 10° C., since the reaction does not progress in the first half of the reaction, unreacted materials are stagnated in the reaction system, and thus there are cases where the reaction rapidly progress. When higher than 50° C., there are cases where color of the lens degenerates. That is, when in a range of the temperature described above, the controllability of the reaction is excellent, further color of the obtained plastic lens is also excellent.

The reaction can be performed for 2 hours to 12 hours, and preferably for 3 hours to 10 hours.

The reaction described above, for example, can be performed as follows. Firstly, after 2-mercaptoethanol and a base are added into water or lower alcohol solvent such as methanol, or ethanol as necessary, epihalohydrin is added dropwise to perform the reaction. It is preferable to adjust so that the reaction temperature and the reaction time are in the ranges described above. Moreover, the reaction time includes the time of adding dropwise of epihalohydrin, and the temperature of the reaction solution needs to be adjusted to the reaction temperature described above when adding dropwise. The used amount of 2-mercaptoethanol is more preferably equal to or more than 1.9 mol and equal to or less than 2.1 mol, with respect to 1 mol of epihalohydrin.

As a base, a metal hydroxide such as sodium hydroxide, potassium hydroxide, a metal carbonate such as sodium carbonate, potassium carbonate, and a tertiary amine such as triethylamine, tributylamine are included, however, sodium hydroxide is most preferable, in the light of the reactivity and the economy. In a case of a monovalent base, the used amount of the base is equal to or more than 0.5 mol and equal to or less than 2 mol, and preferably equal to or more than 0.9 mol and equal to or less than 1.1 mol, with respect to 1 mol of epihalohydrin. In a case of a bivalent base, the half amount of the used amount of a monovalent base is preferable. The base can be used as an aqueous solution, an alcohol solution, or the like, and in a case of using as a solution, the concentration of the base can be appropriately selected.

In addition, except the method described above, by the two-stage reaction in which once diol is produced represented by the following formula (3), thereafter 2-mercaptoethanol is added dropwise, it is also possible to obtain the triol compound represented by the formula (2).

In the method, firstly, 2-mercaptoethanol reacts with an epihalohydrin compound represented by the formula (1) described above to obtain a compound represented by the following formula (3).

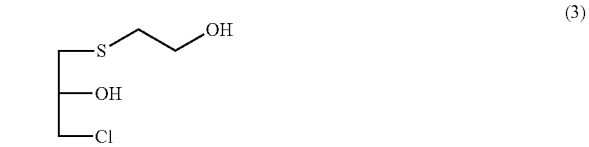

The reaction temperature is from 10° C. to 20° C. The reaction time is from approximately 2 hours to 10 hours.

Next, the compound described above represented by the formula (3) reacts with 2-mercaptoethanol to obtain the triol compound represented by the formula (2). The reaction temperature is from 10° C. to 50° C., preferably 15° C. to 50° C., and more preferably 20° C. to 45° C. The reaction time is from approximately 2 hours to 12 hours.

By performing the steps in a range of the temperature described above, the controllability of the reaction is excellent.

Specifically, the method can be performed as follows.

Firstly, epihalohydrin is added dropwise into a solution comprised of 2-mercaptoethanol, and water or lower alcohol solution such as methanol or ethanol as necessary, and an aqueous solution of the base of the catalyst quantity or lower alcohol such as methanol or ethanol solution of the base of the catalyst quantity. It is preferable to adjust so that the reaction temperature and the reaction time are in the ranges described above. In the solution to which epihalohydrin is added dropwise, the used amount of 2-mercaptoethanol is equal to or more than 1 mol and equal to or less than 3 mol, and preferably equal to or more than 1 mol and equal to or less than 2 mol, with respect to 1 mol of epihalohydrin. In addition, the base described above of the catalyst quantity is used, and in a case of a monovalent base, the used amount of the base described above is equal to or more than 0.001 mol and equal to or less than 0.1 mol, with respect to epihalohydrin. In a case of a bivalent base, the half amount of the used amount of a monovalent base is preferable. The base can be used as an aqueous solution, an alcohol solution, or the like, and in a case of using as a solution, the concentration of the base can be appropriately selected. By epihalohydrin being added dropwise into the solution described above, diol represented by the formula (3) is obtained.

Subsequently, by further adding 2-mercaptoethanol so that 2-mercaptoethanol is equal to or more than 1.5 mol and equal to or less than 3.0 mol, with respect to 1 mol of epihalohydrin if there is any shortage, and by further adding the shortage of the base so that the base is equal to or more than 1.0 mol and equal to or less than 2.0 mol, with respect to epihalohydrin, the polyalcohol compound represented by the formula (2) can be obtained. It is preferable to adjust so that the reaction temperature and the reaction time are in the ranges described above.

In a synthesis of diol represented by the formula (3), in a case where a strong base such sodium hydroxide is used, it is appropriate for the reaction temperature to be set to equal to or more than 10° C. and equal to or less than 50° C. The reaction temperature is too high, since the base added with the catalyst quantity is consumed in a producing reaction of the polyalcohol compound from diol, there is some possibility of decreasing the yield of a diol.

(Step B)

Next, the polyalcohol compound represented by the formula (2) obtained in the step A reacts with thiourea in the presence of hydrogen chloride to obtain the isothiuronium salt.

Specifically, thiourea which is equal to or more than 2.7 mol, preferably equal to or more than 2.7 mol and equal to or less than 6.0 mol, and more preferably equal to or more than 2.9 mol and equal to or less than 3.2 mol, with respect to 1 mol of the polyalcohol compound, is added to the polyalcohol compound represented by the formula (2) to react. The reaction is performed in the presence of hydrogen chloride which is equal to or more than 3 mol, preferably equal to or more than 3 mol and equal to or less than 12 mol, and more preferably equal to or more than 3 mol and equal to or less than 5 mol, with respect to 1 mol of the polyalcohol compound, in a range from room temperature to the reflux temperature, and preferably at the temperature from 90° C. to 120° C., for approximately 1 hour to 10 hours. By the reaction of the polyalcohol compound and thiourea, the isothiuronium salt compound is formed. By using hydrogen chloride, it is possible to obtain the sufficient reaction speed, furthermore, control the coloration of the thiol compound and color of the obtained plastic lens. As hydrogen chloride, a hydrochloric acid aqueous solution and hydrogen chloride gas can be used. In a case of using a hydrochloric acid aqueous solution, the concentration thereof can be appropriately selected.

(Step C)

Aqueous ammonia is added into the reaction solution including the isothiuronium salt obtained in the step B, and the isothiuronium salt is hydrolyzed to obtain the polythiol compound. As a polythiol compound, it is possible to obtain the polythiol composition which is primarily comprised of 4-mercaptomethyl-1,8-dimercapto-3,6-dithiaoctane represented by the following formula (5).

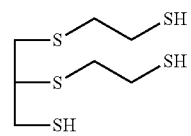

(5)

Specifically, while the reaction solution including the isothiuronium salt is maintained in a range of the temperature from 15° C. to 60° C., preferably from 31° C. to 55° C., more preferably from 31° C. to 45° C., aqueous ammonia is added into the reaction solution for equal to or shorter than 80 minutes, preferably for equal to or shorter than 70 minutes, and more preferably from 20 minutes to 60 minutes. The time of adding aqueous ammonia is preferably shorter, however, the time is set to within the time described above, considering the equipment capacity such as coolability, or the like.

Before adding aqueous ammonia, an organic solvent is preferably added. By adding the organic solvent, the quality such as color of the obtained plastic lens is improved. The additive amount of the organic solvent is appropriately selected according to the classification of the solvent, or the like, however, it is possible to add with the amount which is from 0.1 times to 3.0 times, and preferably from 0.2 times to 1.0 time, with respect to the thiuronium salt reaction solution. As an organic solvent, toluene, xylene, chlorobenzene, dichlorobenzene, and the like are included. Toluene is preferable from the viewpoint of the effect described above.

Aqueous ammonia can be added within the addition time described above so that ammonia (NH$_3$) is equal to or more than 1 mol, preferably equal to or more than 1 mol and equal to or less than 3 mol, and more preferably equal to or more than 1.1 mol and equal to or less than 2 mol, with 1 mol of the used amount of hydrogen chloride described above. The concentration of aqueous ammonia can be set to from 10% to 25%. In addition, ammonia gas can be used instead of aqueous ammonia. In a case where ammonia gas is added in place of all or part of aqueous ammonia, it is possible to perform in the same conditions (the used amount, the addition time, the addition temperature) as aqueous ammonia.

In the present embodiment, ammonia (NH$_3$) is added so that the addition rate is equal to or more than 1.25 mol %/minute, preferably equal to or more than 1.25 mol %/minute and equal to or less than 3.75 mol %/minute, and more preferably equal to or more than 1.38 mol %/minute and equal to or less than 2.5 mol %/minute, with 1 mol of hydrogen chloride. In the step, it is not necessary to continuously add with the rate described above, and the average addition rate in the addition time described above only has to be included in the range.

And, after aqueous ammonia is added, a hydrolysis reaction is continued to be performed in a range from room temperature to the reflux temperature, and preferably from 30° C. to 80° C., for approximately 1 hour to 8 hours.

(Step D)

In the present embodiment, the polythiol composition obtained in the step C is purified by washing.

Specifically, acid washing and then plural times of aqueous washing can be performed. Aqueous washing before acid washing and alkaline washing after acid washing can be performed. It is possible to decrease the number of times of aqueous washing by alkaline washing. By a washing step, it is possible to effectively remove impurities, or the like. By purifying by means of washing, it is possible to produce the plastic lens of high quality in which color of the plastic lens obtained from the polythiol composition is improved, further the occurrence of clouding and striation is decreased, in a satisfactory yield, and the efficiency percentage is also improved. As an example of the preferred aspect, after hydrolyzing, a method of performing aqueous washing, acid washing, aqueous washing, alkaline washing and aqueous washing in order, a method of performing acid washing, aqueous washing, alkaline washing and aqueous washing in order, a method of performing acid washing and aqueous washing in order, and the like can be included. Each washing may be repeated plural times.

Acid washing can be performed by adding hydrochloric acid to the solution including the obtained polythiol composition. The concentration of hydrochloric acid can be set to from 25% to 36%, and preferably 30% to 36%. When the concentration of hydrochloric acid is lower than 25%, there are cases where clouding occurs in the plastic lens by impurities or the like. In addition, the temperature of acid washing can be set to from 10° C. to 50° C., preferably from 15° C. to 50° C., more preferably from 20° C. to 50° C., and even more preferably from 30° C. to 45° C.

For aqueous washing, degassed water in which the concentration of oxygen is equal to or less than 7 mg/L can be used.

As a process of producing degassed water, a method of blowing nitrogen to remove dissolved oxygen, a method of driving out dissolved oxygen by the heat treatment, a method of driving out dissolved oxygen by the vacuum degassing, and the like are included, however, the method is not particularly limited, if the method can make the concentration of oxygen be equal to or less than 5 mg/L.

In this manner, it is possible to effectively suppress color or turbidity which becomes a problem in the optical material such as the plastic lens.

In addition, alkaline washing can be performed by adding an alkaline aqueous solution and stirring in a range from 20° C. to 50° C. for 10 minutes to 3 hours. As an alkaline aqueous solution, aqueous ammonia is preferable. In addition, the concentration of aqueous ammonia can be set to from 0.1% to 10%, preferably 0.1% to 1%, more preferably 0.1% to 0.5%.

Moreover, also in acid washing and alkaline washing, by using water in which the concentration of oxygen is equal to or less than 7 mg/L, it is possible to effectively suppress color or turbidity which becomes a problem in the optical material such as the plastic lens.

After the step D, by performing a step of removing a solvent, a step of removing a low boiling point compound as necessary, a step of filtering, and a step of distilling, it is possible to obtain the polythiol composition including 4-mercaptomethyl-1,8-dimercapto-3,6-dithiaoctane as a polythiol compound.

The step of removing a solvent is a step of removing an organic solvent under normal pressures or reduced pressure, and the decompression degree and the temperature are appropriately selected according to the used solvent or the like, however, it is preferable that the step be performed at 100° C. or less, and preferably 85° C. or less, under reduced pressure.

The step of removing a low boiling point compound is a step of removing the low boiling point compound contained in the target compound under normal pressures or reduced pressure after the step of removing a solvent, and the decompression degree and the temperature are appropriately selected according to the used solvent or the like, however, it is preferable that the step be performed at equal to or lower than 100° C., and preferably equal to or lower than 85° C., under reduced pressure. In doing so, the step may be performed while ventilating inert gas such as nitrogen gas.

The step of filtering is a step of removing by filtering a solid material such as a salt, and a method of filtering and the like are appropriately selected, however, a filtration under reduced pressure or a pressure filtration using a membrane filter or a cartridge filter and the like can be used. It is preferable that the step be performed with a filter which the pore size of a filter is equal to or less than 5 µm, and preferably equal to or less than 2 µm.

The step of distilling is a step of purifying the polythiol compound by distilling, and the decompression degree and the temperature are appropriately selected according to the used solvent or the like, however, it is preferable that the step be performed at equal to or lower than 250° C., and preferably equal to or lower than 200° C., under reduced pressure.

In addition, in order to adjusting the ratio of the peak area of the nitrogen-containing compound (B), a step of reducing the nitrogen-containing compound (B) by purifying by means of acid washing is sometimes employed. In this case, it is necessary to confirm the amount of the nitrogen-containing compound (B) included in the polythiol composition and appropriately set the conditions of acid washing so that the amount of the nitrogen-containing compound (B) is in the predetermined range.

It is considered that the ratio of the peak area of the nitrogen-containing compound (B) is multiply determined by a combination of the conditions over a plurality of steps during synthesizing or purifying. On the other hand, the producing conditions disclosed in the present invention have extremely good repeatability and can provide the polythiol composition including the nitrogen-containing compound (B) in the predetermined range.

Moreover, the process of producing of the present embodiment can also be conducted in the air, however, it is preferable that the process of whole producing be performed under a nitrogen atmosphere in the light of color.

By such a process of producing, the polythiol composition including the polythiol compound (A) and the nitrogen-containing compound (B) with the predetermined range in the present embodiment can be suitably obtained.

[Embodiment II]

In embodiment II, a case of producing "a polythiol compound which is primarily comprised of at least one kind selected from the group consisting of 4,8-dimercaptomethyl- 1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane" is described as follows. Moreover, description of the same steps as an embodiment I will not be repeated.

Hereinafter, each step is described in order.

(Step A)

In the present embodiment, firstly, by 2-mercaptoethanol reacting with an epihalohydrin compound represented by the following formula (1),

(1)

It is possible to obtain a diol compound represented by the following formula (3).

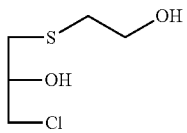
(3)

In the formula (1) described above, X is a halogen atom which is a fluorine atom, a chlorine atom, a bromine atom, or an iodine atom, and preferably a chlorine atom.

In the present embodiment, the reaction can be performed in a range from 2° C. to 30° C., preferably from 5° C. to 20° C., and more preferably from 5° C. to 15° C. The reaction can be performed for 2 hours to 10 hours.

Specifically, the reaction can be performed as follows.

Firstly, epihalohydrin is added dropwise into a solution comprised of 2-mercaptoethanol, and water or lower alcohol solution such as methanol or ethanol as necessary, and an aqueous solution of the above base or lower alcohol such as methanol or ethanol solution of the above base. It is preferable to adjust so that the reaction temperature and the reaction time are in the ranges described above. In the solution to which epihalohydrin is added dropwise, the used amount of 2-mercaptoethanol is equal to or more than 0.5 mol and equal to or less than 3 mol, preferably equal to or more than 0.7 mol and equal to or less than 2 mol, and more preferably equal to or more than 0.9 mol and equal to or less than 1.1 mol, with respect to 1 mol of epihalohydrin. In addition, the base described above of the catalyst quantity is used, and in a case of a monovalent base, the used amount of the base described above is preferably equal to or more than 0.001 mol and equal to or less than 0.1 mol, with respect to 1 mol of epihalohydrin. In a case of a bivalent base, the half amount of the used amount of a monovalent base is preferable. The base can be used as an aqueous solution, an alcohol solution, or the like, and in a case of using as a solution, the concentration of the base can be appropriately selected. By epihalohydrin being added dropwise into the solution described above, diol represented by the formula (3) is obtained.

(Step B)

Next, by the diol compound represented by the formula (3) described above reacting with sodium sulphide, a tetraol compound represented by the following formula (4) can be obtained.

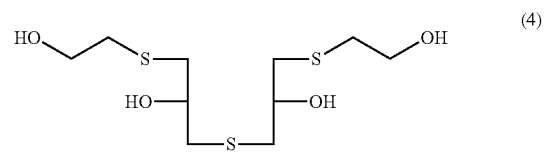 [SMILES: OCCSCC(O)CSCC(O)CSCCO]
(4)

In the present embodiment, the reaction can be performed in a range from 10° C. to 50° C., and preferably from 20° C. to 40° C. The reaction can be performed for 1 hour to 10 hours.

Specifically, the reaction can be performed as follows.

Sodium sulphide aqueous solution is added dropwise or the sodium sulphide solid is charged into the reaction solution including the diol compound after the reaction described above. It is preferable to adjust so that the reaction temperature and the reaction time are in the ranges described above. Sodium sulphide can be used with the amount from 0.4 mol to 0.6 mol, preferably 0.45 mol to 0.57 mol, more preferably 0.48 mol to 0.55 mol, with respect to 1 mol of the diol compound.

(Step C)

Next, by the tetraol compound obtained in the step B and represented by the formula (4) reacting with thiourea in the presence of hydrogen chloride to obtain the isothiuronium salt.

Specifically, thiourea which is equal to or more than 3 mol, preferably equal to or more than 3 mol and equal to or less than 6 mol, and more preferably equal to or more than 4.6 mol and equal to or less than 5.0 mol, with respect to 1 mol of the tetraol compound is added to the tetraol compound to react. The reaction is performed in the presence of hydrogen chloride which is equal to or more than 3.0 mol, and preferably equal to or more than 3 mol and equal to or less than 12 mol, with respect to 1 mol of the tetraol compound in a range from room temperature to the reflux temperature, and preferably at the temperature from 90° C. to 120° C., for approximately 1 hour to 10 hours. By the reaction of the tetraol compound and thiourea, the isothiuronium salt compound is formed. By using hydrogen chloride, it is possible to obtain the sufficient reaction speed, furthermore, control the coloration of a product. As hydrogen chloride, a hydrochloric acid aqueous solution and hydrogen chloride gas can be used.

(Step D)

Aqueous ammonia is added into the reaction solution including the isothiuronium salt obtained in the step C to hydrolyze the isothiuronium salt and the polythiol composition is obtained.

In the present embodiment, as a polythiol compound, it is possible to obtain the polythiol composition including the polythiol compound which is primarily comprised of at least one kind selected from the group consisting of 4,8-dimercaptomethyl-1,11-dimercapto-3,6,9-trithiaundecane represented by the following formula (6), 4,7-dimercaptomethyl-1,11-dimercapto-3,6,9-trithiaundecane represented by the following formula (7), and 5,7-dimercaptomethyl-1,11-dimercapto-3,6,9-trithiaundecane represented by the following formula (8).

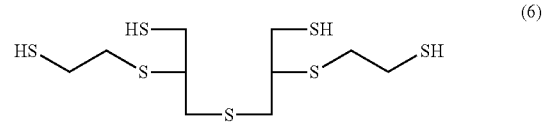
(6)

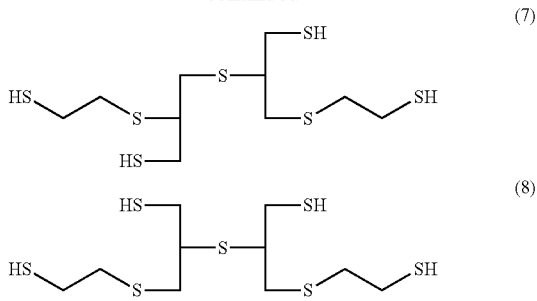

Specifically, while the reaction solution including the isothiuronium salt is maintained in a range of the temperature from 20° C. to 60° C., preferably from 25° C. to 55° C., and more preferably from 25° C. to 50° C., aqueous ammonia is added into the reaction solution for equal to or shorter than 80 minutes, preferably equal to or shorter than 70 minutes, more preferably from 20 minutes to 60 minutes, and even more preferably from 20 minutes to 30 minutes. The time of adding aqueous ammonia is preferably shorter, however, the time is set to within the time described above, considering the equipment capacity such as coolability, or the like.

Before adding aqueous ammonia, an organic solvent is preferably added. By adding the organic solvent, it is possible to suppress to produce a by-product. The additive amount of the organic solvent is appropriately selected according to the classification of the solvent, or the like, however, it is possible to add with the amount which is from 0.1 times to 3.0 times, and preferably from 0.2 times to 2.0 times, with respect to the thiuronium salt reaction solution. As an organic solvent, toluene, xylene, chlorobenzene, dichlorobenzene, and the like are included. Toluene is preferable, from the viewpoint of the effect described above.

Aqueous ammonia can be added within the addition time described above so that ammonia ($NH_3$) is equal to or more than 1 mol, preferably equal to or more than 1 mol and equal to or less than 3 mol, and more preferably equal to or more than 1.1 mol and equal to or less than 2 mol, with 1 mol of the used amount of hydrogen chloride described above. The concentration of aqueous ammonia can be set to from 10% to 25%. In addition, ammonia gas can also be used instead of aqueous ammonia. In a case where ammonia gas is added in place of all or part of aqueous ammonia, it is possible to perform in the same conditions (the used amount, the addition time, the addition temperature) as aqueous ammonia.

In the present embodiment, ammonia ($NH_3$) is added so that the addition rate is equal to or more than 1.25 mol %/minute, preferably equal to or more than 1.25 mol %/minute and equal to or less than 3.75 mol %/minute, and more preferably equal to or more than 1.38 mol %/minute and equal to or less than 2.5 mol %/minute, with respect to 1 mol of hydrogen chloride. In the step, it is not necessary to continuously add with the rate described above, and the average addition rate in the addition time described above has only to be included in the range.

And, after aqueous ammonia is added, a hydrolysis reaction is continued to be performed in a range from room temperature to the reflux temperature, and preferably at the temperature from 30° C. to 80° C., for approximately 1 hour to 8 hours.

(Step E)

In the present embodiment, the polythiol composition obtained in the step D is purified. The step E in the present embodiment can be performed in the same way as embodiment I.

In addition, the step after the step E can also be performed in the same way as Embodiment I.

By such a process of producing, the polythiol composition including the polythiol compound (A) and the nitrogen-containing compound (B) in the predetermined range in the present embodiment can be suitably obtained.

As described above, in the present embodiment, specifically, description of the process of producing the polythiol composition including two types of polythiol compound as the polythiol compound (A) has been given as an example, however, other method can be employed if the ratio of the peak area of the nitrogen-containing compound (B) can be set to the predetermined range.

In addition, for even polythiol compound except the two types selected from the exemplified polythiol compounds described above, by appropriately changing the producing conditions, the ratio of the peak area of the nitrogen-containing compound (B) can be set to the predetermined range.

<Polymerizable Composition for Optical Material>

The polymerizable composition for the optical material in the present embodiment includes the polythiol composition for the optical material which is obtained by the method described above and polyiso(thio)cyanate compound.

The polyiso(thio)cyanate compound is not particularly limited as long as the polyiso(thio)cyanate compound is a compound having at least two or more iso(thio)cyanate groups in one molecule. However, specifically, the polyiso(thio)cyanate includes an aliphatic polyisocyanate compound such as hexamethylene diisocyanate, 1,5-pentane diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl)carbonate, bis(isocyanatoethyl)ether, lysine diisocyanatomethyl ester, or lysine triisocyanate; an alicyclic polyisocyanate compound such as isophorone diisocyanate, bis(isocyanatomethyl)cyclohexane, dicyclohexylmethane diisocyanate, cyclohexane diisocyanate, methylcyclohexane diisocyanate, dicyclohexyldimethylmethane isocyanate, 2,5-bis(isocyanatomethyl)-bicyclo[2.2.1]heptane, 2,6-bis(isocyanatomethyl)-bicyclo[2.2.1]heptane, 3,8-bis(isocyanatomethyl)tricyclodecane, 3,9-bis(isocyanatomethyl)tricyclodecane, 4,8-bis(isocyanatomethyl)tricyclodecane, 4,9-bis(isocyanatomethyl)tricyclodecane, bis(4-isocyanatocyclohexyl)methane, 1,3-bis(isocyanatomethyl)cyclohexane, or 1,4-bis(isocyanatomethyl)cyclohexane; a polyisocyanate compound having an aromatic ring compound such as 1,2-diisocyanatobenzene, 1,3-diisocyanatobenzene, 1,4-diisocyanatobenzene, tolylene diisocyanate, 2,4-diisocyanatotoluene, 2,6-diisocyanatotoluene, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4'-methylenebis(phenyl isocyanate), 4,4'-methylenebis(2-methylphenyl isocyanate), bibenzyl-4,4'-diisocyanate, bis(isocyanatophenyl)ethylene, bis(isocyanatemethyl)benzene, m-xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethylphenyl)ether, bis(isocyanatoethyl)phthalate, or 2,5-di(isocyanatomethyl)furan; a sulfur-containing aliphatic polyisocyanate compound such as bis(isocyanatomethyl)sulfide, bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatoethyl)disulfide, bis(isocyanatopropyl)disulfide, bis(isocyanatomethylthio)methane, bis(isocyanatoethylthio)methane, bis(isocyanatomethylthio)ethane, bis(isocyanatoethylthio)ethane, 1,5-diisocyanato-2-isocyanatomethyl-3-thiapentane, 1,2,3-tris(isocyanatomethylthio)propane, 1,2,3-tris(isocyanatoethylthio)propane, 3,5-dithia-1,2,6,7-heptanetetra isocyanate, 2,6-diisocyanatomethyl-3,5-dithia-1,7-heptane diisocyanate, 2,5-diisocyanate methyl thiophene, or 4-isocyanatoethylthio-2,6-dithia-1,8-octane diisocyanate; an aromatic sulfide-based polyisocyanate compound such as 2-isocyanatophenyl-4-isocyanatophenyl sulfide, bis(4-isocyanatophenyl)sulfide, or bis(4-isocyanatomethylphenyl)sulfide; an aromatic disulfide-based polyisocyanate compound such as bis(4-isocyanatophenyl)disulfide, bis(2-methyl-5-isocyanatophenyl)disulfide, bis(3-methyl-5-isocyanatophenyl)disulfide, bis(3-methyl-6-isocyanatophenyl)disulfide, bis(4-methyl-5-isocyanatophenyl)disulfide, or bis(4-methoxy-3-isocyanatophenyl)disulfide; a sulfur-containing alicyclic polyisocyanate compound such as 2,5-diisocyanato tetrahydrothiophene, 2,5-diisocyanatomethyl tetrahydrothiophene, 3,4-diisocyanatomethyltetrahydrothiophene, 2,5-diisocyanato-1,4-dithiane, 2,5-diisocyanatomethyl-1,4-dithiane, 4,5-diisocyanato-1,3-dithiolane, 4,5-bis(isocyanatomethyl)-1,3-dithiolane, or 4,5-diisocyanatomethyl-2-methyl-1,3-dithiolane; an aliphatic polyisothiocyanate compound such as 1,2-diisothiocyanatoethane or 1,6-diisothiocyanatohexane; an alicyclic polyisothiocyanate compound such as cyclohexane diisothiocyanate; an aromatic polyisothiocyanate compound such as 1,2-diisothiocyanato benzene, 1,3-diisothiocyanato benzene, 1,4-diisothiocyanato benzene, 2,4-diisothiocyanato toluene, 2,5-diisothiocyanato-m-xylene, 4,4'-methylenebis (phenyl isothiocyanate), 4,4'-methylenebis(2-methylphenyl isothiocyanate), 4,4-methylenebis(3-methylphenyl isothiocyanate), 4,4'-diisothiocyanato benzophenone, 4,4'-diisothiocyanato-3,3'-dimethyl benzophenone, or bis(4-isothiocyanatophenyl)ether; furthermore, a carbonyl polyisothiocyanate compound such as 1,3-benzene dicarbonyl diisothiocyanate, 1,4-benzene dicarbonyl diisothiocyanate, or (2,2-pyridine)-4,4-dicarbonyl diisothiocyanate; a sulfur-containing aliphatic polyisothiocyanate compound such as thiobis(3-isothiocyanatopropane), thiobis(2-isothiocyanatoethane), or dithiobis(2-isothiocyanatoethane); a sulfur-containing aromatic polyisothiocyanate compound such as 1-isothiocyanato-4-[(2-isothiocyanato)sulfonyl]benzene, thiobis(4-isothiocyanatobenzene), sulfonyl(4-isothiocyanatobenzene), or dithiobis(4-isothiocyanatobenzene); a sulfur-containing alicyclic polyisothiocyanate compound such as 2,5-diisothiocyanatothiophene, or 2,5-diisothiocyanato-1,4-dithiane; a compound having an isocyanato group and an isothiocyanato group such as 1-isocyanato-6-isothiocyanatohexane, 1-isocyanato-4-isothiocyanatocyclohexane, 1-isocyanato-4-isothiocyanatobenzene, 4-methyl-3-isocyanato-1-isothiocyanatobenzene, 2-isocyanato-4,6-diisothiocyanate-1,3,5-triazine, 4-isocyanatophenyl-4-isothiocyanatophenyl sulfide, or 2-isocyanatoethyl-2-isothiocyanatoethyl disulfide, and the like.

A polyiso(thio)cyanate compound preferably includes an aliphatic-based polyisocyanate compound such as hexamethylene diisocyanate, 1,5-pentanediisocyanate, isophorone diisocyanate, bis(isocyanatomethyl)cyclohexane, dicyclohexylmethane diisocyanate, 2,5-bis(isocyanatomethyl)-bicyclo[2.2.1]heptane, 2,6-bis(isocyanatomethyl)-bicyclo[2.2.1]heptane, bis(4-isocyanatocyclohexyl)methane, 1,3-bis(isocyanatomethyl)cyclohexane, or 1,4-bis(isocyanatomethyl)cyclohexane; a polyisocyanate compound having an aromatic ring compound such as bis(isocyanatomethyl)benzene, m-xylylene diisocyanate, 1,3-diisocyanatobenzene, tolylene diisocyanate, 2,4-diisocyanatotoluene, 2,6-diisocyanatotoluene, 4,4'-methylenebis (phenylisocyanate).

In addition, it is possible to use a halogen substitution thereof such as a chlorine substitution or a bromine substitution, an alkyl substitution thereof, an alkoxy substitution thereof, a nitro substitution thereof, a prepolymer type modified product with polyalcohol, a carbodiimide modified product, a urea modified product, a buret modified product, a reaction product of dimerization or trimerization, and the like. The compounds may be used alone or in a combination of two types or more.

As a polythiol compound used in the polymerizable composition for the optical material, in addition to the polythiol compound for the optical material which is obtained by the method described above, other polythiol compound for the optical material can be used.

Other polythiol compound for the optical material preferably includes an aliphatic polythiol compound such as methane dithiol, 1,2-ethanedithiol, 1,2,3-propanetrithiol, pentaerythritol tetrakis(2-mercaptoacetate), pentaerythritol tetrakis(3-mercaptopropionate), bis(mercaptoethyl)sulfide, 2,5-dimercaptomethyl-1,4-dithiane, tetrakis(mercaptomethylthio methyl)methane, tetrakis(2-mercaptoethylthio methyl)methane, tetrakis(3-mercaptopropylthio methyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane, 1,1,3,3-tetrakis(mercaptomethylthio)propane, 1,1,2,2-tetrakis(mercaptomethylthio)ethane, or 4,6-bis(mercaptomethylthio)-1,3-dithiane.

The usage ratio of the polythiol compound and the polyiso(thio)cyanate compound is not particularly limited, however, the molar ratio is usually within a range of a SH group/a NCO group=0.5 to 3.0, within a range of preferably 0.6 to 2.0, and more preferably 0.8 to 1.3. If the usage ratio is within the range described above, it becomes possible to satisfy a nice balance of various kinds of performance such as the refractive index or the heat resistance demanded as the optical material such as the plastic lens and the transparent material.

For the purpose to improve various properties, the operability, the polymerization reactivity, or the like of the polythiourethane-based resin of the present invention, other substances may be added, in addition to the polythiol compound and the iso(thio)cyanate compound which form an urethane resin. For example, at least one kind of an active hydrogen compound which is typified by amine or the like, a carbonate compound, an ester compound, a metal, a metallic oxide, an organic metal compound, an inorganic substance, or the like may be added, in addition to a urethane forming material.

In addition, in accordance with the purpose, various kinds of substances such as a chain extender, a crosslinking agent, a light stabilizer, an ultraviolet absorber, an antioxidizing agent, an oil color, a filler, or a mold release agent may be added in the same way as a well-known forming process. In order to adjust the desired reaction rate, a well-known reaction catalyst used in producing a thiocarbamic acid s-alkyl ester or a polythiourethane-based resin may be appropriately added. As a reaction catalyst, a well-known reaction catalyst used in producing a thiocarbamic acid S-alkyl ester or a polythiourethane-based resin can be appropriately added.

A reaction catalyst includes dialkyltin halides such as dibutyltin dichloride, or dimethyltin dichloride, dialkyltin dicarboxylates such as dimethyltin diacetate, dibutyltin dioctanoate, or dibutyltin dilaurate, dialkyltin dialkoxides such as dibutyltin dibutoxide, dioctyltin dibutoxide, or dialkyltin dithioalkoxides such as dibutyltin di(thiobutoxide), dialkyltin oxides such as di(2-ethylhexyl)tin oxide, dioctyltin oxide, or bis(butoxy dibutyltin)oxide, dialkyltin sulfides such as dibutyltin sulfide are included. Dialkyltin halides such as dibutyltin dichloride, dimethyltin dichloride, as a preferred example.

Furthermore, as a purpose of modifying a resin, a resin modifying agent such as a hydroxyl compound, an epoxy compound, an episulphide compound, an organic acid and an anhydride thereof, an olefin compound including a (metha) acrylate compound or the like may be added. Here, a resin modifying agent is a compound which adjusts or improves properties of a material comprised of a thiourethane-based resin such as the refractive index, the Abbe number, the heat resistance and the specific gravity, and the mechanical strength thereof such as the impact resistance, or the like.

In addition, the polymerizable composition for the optical material of the present embodiment can include a blueing agent, as necessary. The blueing agent has an absorption band in a wavelength range from orange-colored to yellow-colored in a visible light region and has a function of adjusting color of an optical material comprised of a resin. More specifically, the blueing agent includes a substance showing from blue-colored to purple-colored.

The blueing agent used in the polymerizable composition for the optical material of the present embodiment is not particularly limited, specifically, a dye, a fluorescent brightening agent, a fluorescent pigment, an inorganic pigment and the like are included, however, from among the substances which can be used as a blueing agent, the blueing agent is appropriately selected, according to physical properties which are required for the optical components, resin color, or the like. The blueing agents may be respectively used alone or in a combination two or more kinds.

Among the blueing agents, a dye is preferable, from the viewpoint of the solubility to the polymerizable composition and the viewpoint of the transparency of the optical material which is obtained.

From the viewpoint of the absorption wavelength, it is preferred that a dye in which the maximum absorption wavelength is equal to or more than 520 nm and equal to or less than 600 nm is used. It is more preferred that a dye in which the maximum absorption wavelength is equal to or more than 540 nm and equal to or less than 580 nm is used.

In addition, an anthraquinone-based dye is preferable, from the viewpoint of the structure of the compound.

A method of adding the blueing agent is not particularly limited, and it is desired to add to a monomer system in advance. As method, various kinds of methods such as a method of being dissolved in a monomer or a method in which a master solution containing the high concentration of the blueing agent is prepared and the master solution is diluted by a monomer or other additive agent which is used to be added can be employed.

The polymerizable composition for the optical material of the present embodiment is obtained as a mixed liquid, specifically, by mixing the polythiol composition obtained by the process of producing described above and the polyiso (thio)cyanate compound, furthermore other components as necessary. The mixed liquid is put into a mold and is usually, gradually heated from a low temperature to a high temperature to be polymerized after degassing by an appropriate method as necessary.

In this manner, a molded product comprised of the polythiourethane-based resin obtained by curing the polymerizable composition of the present embodiment has characteristics which are the high refractive index, the low dispersion, excellent heat resistance and durability, light weigh, and excellent impact resistance, furthermore, color is favorable and it is suitable as the optical material such as a spectacle lens, a camera lens and the transparent material element.

In addition, the plastic lens obtained by using the polythiourethane-based resin of the present embodiment may be subjected to a physical or chemical treatment such as the surface polishing, the antistatic treatment, the hard coat treatment, the antireflection coat treatment, the dyeing treatment, the dimming treatment as necessary, in order to perform an improvement of anti-reflection, imparting high hardness, enhancing abrasive resistance, enhancing chemical resistance, imparting antifog properties, imparting fashionability, or the like.

EXAMPLES

Hereinafter, more detailed description will be given of the present invention according to Examples, however, the present invention is not limited thereto.

Moreover, in the following Examples, properties were measured by the following methods of measurement.

Specific gravity: measured in conformity to JIS K 0061.

APHA: APHA is a method of displaying color and determined by using a standard solution which was prepared by dissolving a reagent of platinum and cobalt and comparing the standard solution diluted solution having the concentration equal to the color of samples, the "frequency" was set to the measured value.

The amount of water: A monomer was dissolved in toluene, and the water measurement was conducted by Karl Fischer Moisture Titrate.

Viscosity: It was measured in accordance with JIS K 7117.

Refractive index: It was measured at 20° C. by RA-600 digital refractometer manufactured by KYOTO ELECTRONICS MANUFACTURING CO., LTD.

Ammonium content: A monomer was dissolved in chloroform, extracted by water and measured by an ion chromatography.

Acid content: A monomer was dissolved in a solvent, calculated as the HCl content by titrating by a methanol solution of KOH.

Loss degree of transparency of resin: A flat plate of 9 mm was produced with the producing conditions of the plastic lenses of Examples to measure by a loss degree of transparency measuring apparatus (manufactured by HAYASHI WATCH-WORKS: LUMINAR ACE LA-150SE).

Resin YI: It is a yellow index in the evaluation of color. YI is measured by a color-difference meter. A flat plate of 9 mm was produced with the producing conditions of the plastic lenses of Examples to measure a YI value using a color-difference meter (CR-400) manufactured by KONICA MINOLTA, INC.

Striation: The lens was produced with the producing conditions of the plastic lenses of Examples and visually observed under a high-pressure mercury lamp, and the lens in which a stripe-like pattern was not observed was 0 and the lens in which a stripe-like pattern was observed was X.

In addition, dissolved oxygen was turned out of water by blowing hydrogen into water to obtain degassed water which is 2 ppm of the concentration of dissolved oxygen.

Example A-1

Synthesis of Polythiol Composition which is Primarily Comprised of 4-mercaptomethyl-1,8-dimercapto-3,6-dithiaoctane 124.6 parts by weight of 2-mercaptoethanol and 18.3 parts by weight of degassed water (the concentration of dissolved oxygen is 2 ppm) were charged into a reaction vessel. After 101.5 parts by weight of 32% by weigh of sodium hydroxide aqueous solution was added dropwise and charged from 12° C. to 35° C. over 40 minutes, 73.6 parts by weight of epichlorohydrin was added dropwise and charged from 29° C. to 36° C. over 4.5 hours, and continuously, stirring was performed for 40 minutes. From an NMR data, the production of 1,3-bis(2-hydroxyethylthio)-2-propanol was confirmed.

331.5 parts by weight of 35.5% hydrochloric acid was charged, and subsequently, 183.8 parts by weight of the purity of 99.90% of thiourea was charged and stirred at 110° C. for 3 hours under reflux to convert into a thiuronium salt. After cooling to 45° C., 320.5 parts by weight of toluene was added and cooled to 31° C., 243.1 parts by weight of 25% by weight of ammonia aqueous solution was charged from 31° C. to 41° C. over 44 minutes and stirred from 54° C. to 62° C. for 3 hours, and a toluene solution of the polythiol composition which is primarily comprised of 4-mercaptomethyl-1,8-dimercapto-3,6-dithiaoctane was obtained. 162.8 parts by weight of 35.5% hydrochloric acid was added into the toluene solution and acid washing was performed from 35° C. to 43° C. for 1 hour. 174.1 parts by weight of degassed water (the concentration of dissolved oxygen is 2 ppm) was added and washing which was performed from 35° C. to 45° C. for 30 minutes was conducted twice. 162.1 parts by weight of 0.1% aqueous ammonia was added to wash for 30 minutes. 174.2 parts by weight of degassed water was added and washing which was performed from 35° C. to 45° C. for 30 minutes was conducted twice. After toluene and trace water were removed under heating and reduced pressure, filtration under reduced pressure was performed by PTFE type membrane filter of 1.2 μm to obtain 205.0 parts by weight of a polythiol composition which is primarily comprised of 4-mercaptomethyl-1,8-dimercapto-3,6-dithiaoctane. Physical properties of the obtained polythiol composition are shown in Table-1.

The results of an elementary analysis and a NMR analysis of 4-mercaptomethyl-1,8-dimercapto-3,6-dithiaoctane are shown.

Elementary analysis (as $C_7H_{16}S_5$)

CHS analysis value 32.12 6.19 61.69 Calculated value 32.27 6.19 61.53 $^1$H NMR ($CDCl_3$)

$\delta_{ppm}$=1.74 to 1.91 (3H, m, SH)

2.70 to 3.00 (13H, m, CH)

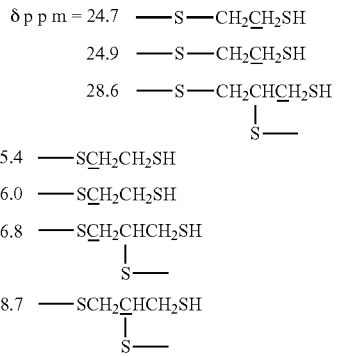

$^{13}$C NMR (in $CDCl_3$)

$\delta ppm$ = 24.7 —S—$CH_2CH_2$SH
24.9 —S—$CH_2\underline{C}H_2$SH
28.6 —S—$CH_2\underline{C}HCH_2$SH
               |
               S—
35.4 —S$\underline{C}H_2CH_2$SH
36.0 —S$\underline{C}H_2CH_2$SH
36.8 —S$\underline{C}H_2CHCH_2$SH
               |
               S—
48.7 —S$CH_2\underline{C}HCH_2$SH
               |
               S—

(Purification and Structure Confirmation)

By a silica gel column chromatography (toluene-methanol, stepwise method) was repeatedly performed, a nitrogen-containing compound (referred to as B-1) was fractionated and purified from the polythiol composition which is primarily comprised of 4-mercaptomethyl-1,8-dimercapto-3,6-dithiaoctane.

From the results of instrumental analysis, it was identified that the nitrogen-containing compound (B-1) had a structure in which one of a mercapto group of 4-mercaptomethyl-1, 8-dimercapto-3,6-dithiaoctane was replaced with a group represented by the following formula (a), furthermore other one of a mercapto group was replaced with a hydroxyl group. In the following formula (a), * represents an atomic bonding.

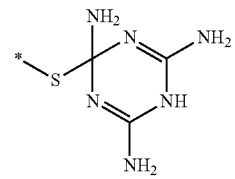

(a)

(1) Mass Spectrum

FAB-MS: m/z 370 (M$^+$) (Matrix m-NBA)

(2) IR (Universal ATR Method):

3300 cm$^{-1}$: NH stretching, 2541 cm$^{-1}$: SH stretching, 1606 cm$^{-1}$: C=N stretching, 1520 cm$^{-1}$: NH vending.

(3) $^1$H-NMR (DMSO-d$_6$):

δ ppm 2.3-2.9 (11H (—CH$_2$—, SH))), 3.1-3.45 (3H (—CH—, CH$_2$OH)), 6.6-6.8 (6H(NH$_2$)).

(4)$^{13}$C-NMR (DMSO-d$_6$):

δ ppm 24-40 (CH$_2$), 46-48 (CH), 70.3 (C—OH(C adjacent to O)), 166.5, 178.1 (—C—N— (melamine skeleton)).

The ratio of the peak area of the nitrogen-containing compound (B-1) to 4-mercaptomethyl-1,8-dimercapto-3,6-dithiaoctane (referred to as a polythiol compound (A-1)) was determined in the following manner.

1. Measurement Conditions of High Performance Liquid Chromatography

Column: YMC-Pack ODS-A A-312 (S5Φ6 mm×150 mm)

Mobile phase: acetonitrile/0.01 mol-potassium dihydrogen phosphate aqueous solution=60/40 (vol/vol)

Column temperature: 40° C.

Flow rate: 1.0 ml/min

Detector: UV detector, wavelength 230 nm

Preparation of measurement solution: 160 mg of a sample is dissolved and mixed in 10 ml of acetonitrile.

Injection volume: 2 μL

2. Ratio of the Peak Area of Nitrogen-Containing Compound (B-1)

In the polythiol composition which was produced in Example A-1, the ratio of the peak area of the nitrogen-containing compound (B-1) to the polythiol compound (A-1) was calculated using the following expression.

{[peak area of nitrogen-containing compound (B-1)]/ [peak area of polythiol compound (A-1)]}×100    Expression The result calculated using the expression for computation described above was 0.21.

Moreover, the retention times of the polythiol compound (A-1) and the nitrogen-containing compound (B-1) were as follows. A chart of high performance liquid chromatography is shown in FIG. 1.

Polythiol compound (A-1): From 12.0 minutes to 13.5 minutes.

Nitrogen-containing compound (B-1): From 4.3 minutes to 5.6 minutes.

(Manufacturing of Plastic Lens)

52 parts by weight of m-xylylene diisocyanate, 0.015 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by CHEMICAL CO., LTD.; ultraviolet absorbing agent) were mixed and dissolved at 20° C. 48 parts by weight of the obtained polythiol composition which is primarily comprised of the polythiol compound (A-1) was charged and mixed to set to a mixed homogeneous liquid. After the homogeneous liquid was degassed at 600 Pa for 1 hour, the homogeneous liquid was put into a mold die consisting of a glass mold and a tape after filtrating using a Teflon (registered trademark) filter of 1 μm. The mold die was put into an oven, gradually heated up from 10° C. to 120° C., and polymerized for 20 hours. After the polymerization was finished, the mold die was taken out from the oven to obtain a resin by releasing from the mold die. The obtained resin was further annealed at 120° C. for 3 hours. Physical properties of the obtained plastic lens are shown in Table-1.

Examples A-2 to A-10

The polythiol composition which is primarily comprised of the polythiol compound (A-1) in the same way as Example A-1 except setting to the producing conditions described in Table-1 was produced and the plastic lens was manufactured. The results are shown in Table-1.

Example B-1

Synthesis of Polythiol Composition which is Primarily Comprised of 4-mercaptomethyl-1,8-dimercapto-3,6-dithiaoctane 124.6 parts by weight of 2-mercaptoethanol and 18.3 parts by weight of degassed water (the concentration of dissolved oxygen is 2 ppm) were charged into a reaction vessel. After 101.5 parts by weight of 32% by weigh of sodium hydroxide aqueous solution was added dropwise and charged from 12° C. to 35° C. over 40 minutes, 73.6 parts by weight of epichlorohydrin was added dropwise and charged from 28° C. to 36° C. over 4.5 hours, and continuously, stirring was performed for 40 minutes. From NMR data, the production of 1, 3-bis(2-hydroxyethylthio)-2-propanol was confirmed. Next, 183.7 parts by weight of the purity of 99.90% of thiourea was charged, 108.6 parts by weight of the purity of 90.7% of hydrochloric acid gas was blown and stirred at 110° C. for 3 hours under reflux to convert into a thiuronium salt. After cooling to 45° C., 320.5 parts by weight of toluene was added and cooled to 31° C., 216.7 parts by weight of 25% by weight of aqueous ammonia solution was charged from 31° C. to 40° C. over 29 minutes and matured from 54° C. to 63° C. for 3 hours, and a toluene solution of the polythiol composition which is primarily comprised of 4-mercaptomethyl-1,8-dimercapto-3,6-dithiaoctane was obtained. 162.9 parts by weight of 35.5% hydrochloric acid was added into the toluene solution and acid washing was performed from 34° C. to 43° C. for 1 hour. 174.2 parts by weight of degassed water (the concentration of dissolved oxygen is 2 ppm) was added and washing which was performed from 35° C. to 45° C. for 30 minutes was conducted twice. 162.8 parts by weight of 0.1% aqueous ammonia was added to wash for 30 minutes. 174.2 parts by weight of degassed water (the concentration of dissolved oxygen is 2 ppm) was added and washing which was performed from 34° C. to 43° C. for 30 minutes was conducted twice. After toluene and trace water were removed under heating and reduced pressure, filtration under reduced pressure was performed by PTFE type membrane filter of 1.2 μm to obtain 205.0 parts by weight of polythiol composition which is primarily comprised of 4-mercaptomethyl-1,8-dimercapto-3,6-dithiaoctane (a polythiol compound (A-1)). Physical properties of the obtained polythiol composition are shown in Table-1.

The identification of 4-mercaptomethyl-1,8-dimercapto-3,6-dithiaoctane was performed in the same way as Example A-1 and the same results were obtained.

(Purification and Structure Confirmation)

By a silica gel column chromatography (toluene-methanol, stepwise method) was repeatedly performed, the nitrogen-containing compound (B-1) was fractionated and purified from the polythiol composition which is primarily comprised of polythiol compound (A-1).

From the results of instrumental analysis, it was identified that the nitrogen-containing compound (B-1) had a structure in which one of a mercapto group of 4-mercaptomethyl-1,8-dimercapto-3,6-dithiaoctane was replaced with a group represented by the following formula (a), furthermore other one of a mercapto group was replaced with a hydroxyl group. In the following formula (a), * represents an atomic bonding.

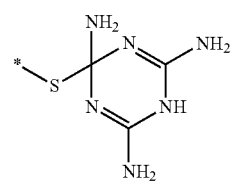

(a)

(1) Mass Spectrum

FAB-MS: m/z 370 (M$^+$) (Matrix m-NBA)

(2) IR (Universal ATR Method):

3300 cm$^{-1}$: NH stretching, 2541 cm$^{-1}$: SH stretching, 1606 cm$^{-1}$: C=N stretching, 1520 cm$^{-1}$: NH vending.

(3) $^1$H-NMR (DMSO-d$_6$):

δ ppm 2.3-2.9 (11H (—CH$_2$—, SH))), 3.1-3.45 (3H (—CH—, CH$_2$OH)), 6.6-6.8 (6H(NH$_2$)).

(4) $^{13}$C-NMR (DMSO-d$_6$):

δ ppm 24-40 (CH$_2$), 46-48 (CH), 70.3 (C—OH(C adjacent to O)), 166.5, 178.1 (—C—N— (melamine skeleton)).

The ratio of the peak area of the nitrogen-containing compound (B-1) to 4-mercaptomethyl-1,8-dimercapto-3,6-dithiaoctane (referred to as a polythiol compound (A-1)) was determined by performing in the same way as Example A-1.

(Manufacturing Plastic Lens)

52 parts by weight of m-xylylene diisocyanate, 0.015 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by KYODO CHEMICAL CO., LTD.; ultraviolet absorbing agent) were mixed and dissolved at 20° C. 48 parts by weight of the polythiol composition which is primarily comprised of the obtained polythiol compound (A-1) was charged and mixed to set to a mixed homogeneous liquid. After the homogeneous liquid was degassed at 600 Pa for 1 hour, the homogeneous liquid was put into a mold die consisting of a glass mold and a tape after filtrating using a Teflon (registered trademark) filter of 1 μm. The mold die was put into an oven, gradually heated up from 10° C. to 120° C., and polymerized for 20 hours. After the polymerization was finished, the mold die was taken out from the oven to obtain a resin by releasing from the mold die. The obtained resin was further annealed at 120° C. for 3 hours. Physical properties of the obtained lens are shown in Table-1.

Examples B-2 to B-10

The polythiol composition which is primarily comprised of the polythiol compound (A-1) in the same way as Example B-1 except setting to the producing conditions described in Table-1 was produced and the plastic lens was manufactured. The results are shown in Table-1.

TABLE 1

| | Condition I | Condition II | | Condition III | | Analysis value of monomer | | | | | | | Ratio of peak area of nitrogen-containing compound | Evaluation of resin | | |
|---|---|---|---|---|---|---|---|---|---|---|---|---|---|---|---|---|
| | Adding dropwise temperature °C. | Charging temperature °C. | Charging time Minute | Acid concentration % | Acid washing temperature °C. | Color | Specific Gravity | Acidity ppm | Water ppm | Viscosity mPa·s | Refractive index | NH$_4$ ppm | | Color YI | loss degree of transparency % | Striation |
| Example A-1 | 29-36 | 31-41 | 44 | 35.5 | 35-43 | 10 | 1.257 | 10 | 70 | 32 | 1.6310 | 0.02 | 0.21 | 4.2 | 15 | ○ |
| Example A-2 | 28-39 | 31-41 | 52 | 35.5 | 34-40 | 10 | 1.256 | 10 | 30 | 33 | 1.6308 | 0.01 | 0.20 | 4.3 | 18 | ○ |
| Example A-3 | 29-39 | 31-41 | 42 | 35.5 | 34-43 | 10 | 1.256 | 12 | 50 | 34 | 1.6308 | 0.02 | 0.18 | 4.3 | 18 | ○ |
| Example A-4 | 28-36 | 31-41 | 56 | 35.5 | 35-44 | 10 | 1.257 | 11 | 60 | 33 | 1.6309 | 0.05 | 0.20 | 4.3 | 18 | ○ |
| Example A-5 | 29-38 | 31-40 | 57 | 35.5 | 35-44 | 10 | 1.256 | 12 | 120 | 33 | 1.6308 | 0.05 | 0.26 | 4.0 | 17 | ○ |
| Example A-6 | 29-32 | 31-42 | 53 | 35.5 | 34-43 | 10 | 1.255 | 13 | 80 | 33 | 1.6310 | 0.06 | 0.19 | 4.0 | 18 | ○ |
| Example A-7 | 29-41 | 31-42 | 37 | 35.5 | 35-44 | 10 | 1.256 | 12 | 110 | 33 | 1.6309 | 0.04 | 0.24 | 3.9 | 17 | ○ |
| Example A-8 | 29-37 | 31-41 | 55 | 35.5 | 34-44 | 10 | 1.257 | 7 | 20 | 33 | 1.6312 | 0.02 | 0.17 | 4.2 | 17 | ○ |
| Example A-9 | 28-40 | 31-40 | 47 | 30 | 34-44 | 10 | 1.257 | 8 | 20 | 33 | 1.6312 | 0.02 | 0.17 | 4.2 | 17 | ○ |
| Example A-10 | 28-41 | 31-41 | 36 | 30 | 35-43 | 10 | 1.257 | 8 | 20 | 33 | 1.6313 | 0.03 | 0.20 | 4.4 | 18 | ○ |
| Example B-1 | 28-36 | 31-40 | 29 | 35.5 | 34-43 | 10 | 1.256 | 14 | 160 | 33 | 1.6312 | 0.04 | 0.26 | 4.4 | 17 | ○ |
| Example B-2 | 29-41 | 31-40 | 37 | 35.5 | 35-43 | 10 | 1.256 | 20 | 50 | 33 | 1.6315 | 0.01 | 0.29 | 4.5 | 18 | ○ |
| Example B-3 | 28-37 | 31-40 | 35 | 35.5 | 35-43 | 10 | 1.256 | 19 | 20 | 33 | 1.6311 | 0.02 | 0.28 | 4.3 | 17 | ○ |
| Example B-4 | 28-39 | 31-39 | 38 | 35.5 | 35-43 | 10 | 1.256 | 19 | 70 | 33 | 1.6309 | 0.02 | 0.31 | 4.2 | 18 | ○ |
| Example B-5 | 28-40 | 31-39 | 37 | 35.5 | 35-43 | 10 | 1.256 | 19 | 60 | 33 | 1.6306 | 0.01 | 0.33 | 4.3 | 19 | ○ |
| Example B-6 | 27-40 | 31-40 | 31 | 35.5 | 35-43 | 10 | 1.256 | 16 | 50 | 33 | 1.6309 | 0.01 | 0.29 | 4.3 | 18 | ○ |
| Example B-7 | 25-36 | 31-40 | 33 | 35.5 | 35-42 | 10 | 1.256 | 15 | 50 | 33 | 1.6309 | 0.04 | 0.29 | 4.2 | 18 | ○ |
| Example B-8 | 29-38 | 31-39 | 32 | 35.5 | 35-42 | 10 | 1.256 | 17 | 60 | 33 | 1.6309 | 0.04 | 0.26 | 4.3 | 18 | ○ |

TABLE 1-continued

| | Condition I | Condition II | | Condition III | | Analysis value of monomer | | | | | | | Ratio | Evaluation of resin | | |
|---|---|---|---|---|---|---|---|---|---|---|---|---|---|---|---|---|
| | Adding dropwise temperature °C. | Charging temperature °C. | Charging time Minute | Acid concentration % | Acid washing temperature °C. | Color | Specific Gravity | Acidity ppm | Water ppm | Viscosity mPa·s | Refractive index | NH$_4$ ppm | of peak area of nitrogen-containing compound | Color YI | loss degree of transparency % | Striation |
| Example B-9 | 29-40 | 31-39 | 21 | 30 | 35-42 | 10 | 1.256 | 16 | 20 | 33 | 1.6312 | 0.02 | 0.30 | 4.3 | 18 | ○ |
| Example B-10 | 29-39 | 31-38 | 38 | 30 | 35-43 | 10 | 1.256 | 16 | 20 | 33 | 1.6313 | 0.01 | 0.28 | 4.3 | 19 | ○ |

Condition I: Conditions of reacting 2-mercaptoethanol with epichlorohydrin.
Condition II: Conditions of charging an ammonia aqueous solution in a hydrolysis reaction.
Condition III: Conditions of hydrochloric acid washing.
Ratio of peak area of nitrogen-containing compound: Expression {[peak area of nitrogen-containing compound (B-1)]/[peak area of polythiol compound (A-1)]} × 100

Examples I-1 to I-4, Comparative Example I-1

Preparation of Thiol Composition Added the Predetermined Amount of Nitrogen-Containing Compound (B-1)

The predetermined amount of the nitrogen-containing compound (B-1) which was fractionated in advance was added to the polythiol composition that is primarily comprised of the polythiol compound (A-1), the ratio of the peak area of the nitrogen-containing compound (B-1) to the polythiol compound (A-1) was analyzed by high performance liquid chromatography in accordance with the conditions described above. The results are shown in Table-2.

(Viscosity Measurement of Polymerizable Composition)

The producing time of the polymerizable composition was set to 0 hour and the viscosity after 7 hours was evaluated as an index.

52 parts by weight of m-xylylene diisocyanate, 0.015 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by KYODO CHEMICAL CO., LTD.; ultraviolet absorbing agent) were mixed and dissolved at 20° C. 48 parts by weight of the polythiol composition which is primarily comprised of the obtained polythiol compound (A-1) was charged and mixed to set to a mixed homogeneous liquid. The producing time of the mixed homogeneous solution was set to 0 hour and the viscosity after 7 hours was evaluated by a Brookfield type viscometer. The results are shown in Table-2.

(Manufacturing Plastic Lens)

52 parts by weight of m-xylylene diisocyanate, 0.015 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by KYODO CHEMICAL CO., LTD.; ultraviolet absorbing agent) were mixed and dissolved at 20° C. 48 parts by weight of the polythiol composition which is primarily comprised of the obtained polythiol compound (A-1) was charged and mixed to set to a mixed homogeneous liquid. Then, the homogeneous liquid was degassed at 600 Pa for 1 hour, the homogeneous liquid was put into a mold die consisting of a glass mold and a tape after filtrating using a Teflon (registered trademark) filter of 1 μm. The mold die was put into an oven, gradually heated up from 10° C. to 120° C., and polymerized for 20 hours. After the polymerization was finished, the mold die was taken out from the oven to obtain a resin by releasing from the mold die. The obtained resin was further annealed at 120° C. for 3 hours. Physical properties of the obtained plastic lens are shown in Table-2.

TABLE 2

| | | Ratio of peak area of nitrogen-containing compound (B-1) | Viscosity after 7 hours (mPa·s) | Evaluation of resin | | |
|---|---|---|---|---|---|---|
| | | | | Color YI | loss degree of transparency % | Striation |
| Example | I-1 | 0.8 | 44 | 4.6 | 19 | ○ |
| | I-2 | 1.2 | 50 | 4.6 | 19 | ○ |
| | I-3 | 1.8 | 84 | 4.5 | 22 | ○ |
| | I-4 | 2.8 | 117 | 4.5 | 23 | ○ |
| Comparative Example | I-1 | 3.2 | 1000< | 4.3 | 25 | x |

The ratio of the peak area of the nitrogen-containing compound Expression: {[peak area of nitrogen-containing compound (B-1)]/[peak area of polythiol compound (A-1)]} × 100

From the results described above, in a case where the ratio of the peak area of the nitrogen-containing compound (B-1) to the polythiol compound (A-1) was equal to or less than 3.0 as Examples I-1 to 1-4, color and the loss degree of transparency were excellent and striation also did not occur. Furthermore, the viscosity of the polymerizable composition after 7 hours was low and handling characteristics were excellent.

On the other hand, in a case where the ratio of the peak area of the nitrogen-containing compound (B-1) was over 3.0 as Comparative Example I-1, since the viscosity of the polymerizable composition after 7 hours was over 1,000 mPa·s, it became clear that manufacturing stability of the plastic lens was also affected.

Example C-1

Synthesis of Polythiol Composition which is Primarily Comprised of bis(mercaptomethyl)-3,6,9-trithia-1,11-undecanedithiol 51.2 parts by weight of 2-mercaptoethanol, 26.5 parts by weight of degassed water (the concentration of dissolved oxygen is 2 ppm), and 0.16 parts by weight of 49% by weight sodium hydroxide aqueous solution were charged into a reaction vessel. 61.99 parts by weight of epichlorohydrin was added dropwise and charged from 9° C. to 11° C. over 6.5 hours, and continuously, stirring was performed for 60 minutes. From an NMR data, the production of 1-chloro-3-(2-hydroxyethylthio)-2-propanol was confirmed.

Next, 150.0 parts by weight of 17.3% sodium sulphide aqueous solution was added dropwise and charged from 7° C. to 37° C. over 5.5 hours and stirred for 120 minutes. From an NMR data, the production of a tetraol compound of the formula (4) was confirmed. Then, 279.0 parts by weight of 35.5% hydrochloric acid was charged, and then 125.8 parts by weight of the purity of 99.90% of thiourea was charged and stirred at 110° C. for 3 hours under reflux to convert into a thiuronium salt. After cooling to 45° C., 214.0 parts by weight of toluene was added and cooled to 26° C., 206.2 parts by weight of 25% by weight aqueous ammonia solution was charged from 26° C. to 50° C. over 30 minutes and stirred from 50° C. to 65° C. for 1 hour, and a toluene solution of the polythiol composition which is primarily comprised of 4,8-dimercaptomethyl-1,11-dimercapto-3,6,9-trithiaundecane, 4,7-dimercaptomethyl-1,11-dimercapto-3,6,9-trithiaundecane and 5,7-dimercaptomethyl-1,11-dimercapto-3,6,9-trithiaundecane was obtained. The toluene solution was added into 59.4 parts by weight of 36% hydrochloric acid and acid washing which was performed from 34° C. to 39° C. for 30 minutes was conducted twice. 118.7 parts by weight of degassed water (the concentration of dissolved oxygen is 2 ppm) was added and washing which was performed from 35° C. to 45° C. for 30 minutes was conducted five times. After toluene and trace water were removed under heating and reduced pressure, filtration under reduced pressure was performed by PTFE type membrane filter of 1.2 µm to obtain 115.9 parts by weight of the polythiol composition which is primarily comprised of 4,8-dimercaptomethyl-1,11-dimercapto-3,6,9-trithiaundecane (hereinafter, compound A), 4,7-dimercaptomethyl-1,11-dimercapto-3,6,9-trithiaundecane (hereinafter, compound B), and 5,7-dimercaptomethyl-1,11-dimercapto-3,6,9-trithiaundecane (hereinafter, compound C) (an isomer mixture of compound A/B/C=85/5/10 (molar ratio)). Physical properties of the obtained polythiol composition are shown in Table-3.

Polythiol comprised of the isomers was respectively isolated and identified by reversed phase chromatography. Firstly, the results of elementary analysis, IR, MS and NMR of the compound A are shown.

<Elementary Analysis>

|   | Measured value (%) | Calculated value (%) |
|---|---|---|
| C | 32.7 | 32.8 |
| H | 6.2 | 6.1 |
| S | 61.1 | 61.2 |

<IR $\nu_{max}$ (KBr) cm$^{-1}$>2543 (SH)
<MS> m/z=366 (M$^+$)

<$^{13}$C-NMR CDCl$_3$>

| | δ ppm |
|---|---|
| | $a_1$ = 24.9 |
| | $a_2$ = 35.1 |
| | $a_3$ = 28.5 |
| | $a_4$ = 48.7 |
| | $a_5$ = 35.9 |

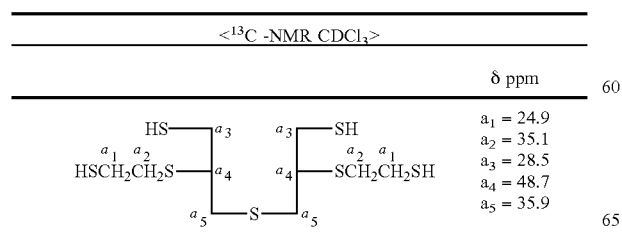

Next, the results of NMR of the compound C are shown. The results of elementary analysis, IR and MS were the same as the compound A.

<$^{13}$C-NMR CDCl$_3$>

| | δ ppm |
|---|---|
| | $c_1$ = 24.7 |
| | $c_2$ = 35.5 |
| | $c_3$ = 36.8 |
| | $c_4$ = 49.4 |
| | $c_5$ = 28.6 |

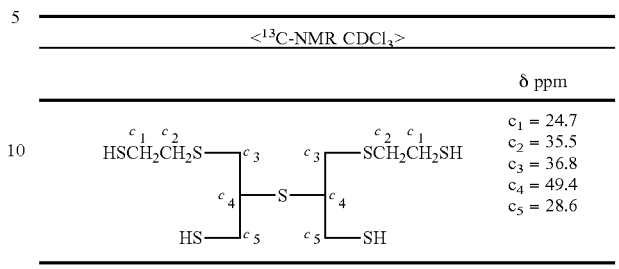

Lastly, the results of NMR of the compound B are shown. The results of elementary analysis, IR and MS were the same as the compound A.

<$^{13}$C-NMR CDCl$_3$>

| | δ ppm |
|---|---|
| | $b_1$ = 24.9 |
| | $b_2$ = 35.1 |
| | $b_3$ = 28.5 |
| | $b_4$ = 48.7 |
| | $b_5$ = 35.9 |
| | $b_6$ = 28.6 |
| | $b_7$ = 49.4 |
| | $b_8$ = 36.8 |
| | $b_9$ = 35.5 |
| | $b_{10}$ = 24.7 |

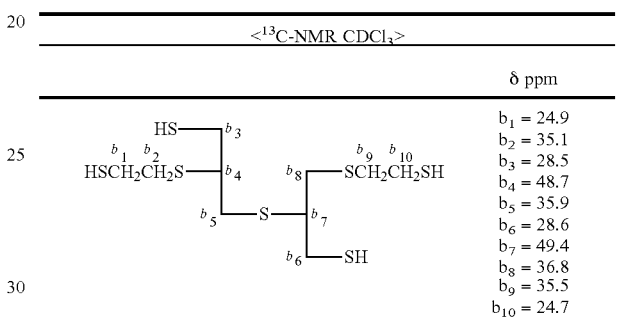

(Fractionation and Structure Confirmation)

The nitrogen-containing compound (referred to as B-2) included in the polythiol composition was fractionated from the polythiol composition which is primarily comprised of the polythiol compound (referred to as A-2) comprised of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane by performing preparative high performance liquid chromatography.

From the results of instrumental analysis, it was proved that the nitrogen-containing compound (B-2) had a structure in which one of a mercapto group of the polythiol compound (A-2) consisting of 5,7-dimercaptomethyl-1,11-dimercapto-3,6,9-trithiaundecane 4,7-dimercaptomethyl-1,11-dimercapto-3,6,9-trithiaundecane, and 4,8-dimercaptomethyl-1,11-dimercapto-3,6,9-trithiaundecane was replaced with a group represented by the following formula (a), furthermore, other one of a mercapto group was replaced with a hydroxyl group. In the following formula (a), * represents an atomic bonding.

The results of an analysis of the nitrogen-containing compound (B-2) included in the polythiol composition are shown.

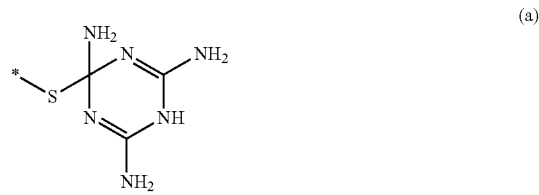 [SMILES: *SC1(N)N=C(N)NC(N)=N1]

(a)

(1) Mass Spectrum
FAB-MS: m/z 476 (M$^+$) (Matrix m-NBA)
(2) IR (Universal ATR Method):
3329, 3198 cm$^{-1}$: NH stretching, 2539 cm$^{-1}$: SH stretching, 1606 cm$^{-1}$: C=N stretching, 1525 cm$^{-1}$: NH vending.
(3) $^1$H-NMR (CDCl$_3$):
δ ppm 1.6-1.8 (4H(SH)), 2.5-3.5 (33H (—CH$_2$—, —CH—)), 3.8-3.9 (3H (—CHOH, CH$_2$OH)).
(4) $^{13}$C-NMR (CDCl$_3$):
δ ppm 25-39 (CH$_2$), 48-50 (CH), 61 (CH$_2$—OH (C adjacent to O), 69-70 (CH—OH (C adjacent to O)), 166, 180 (—C—N— (C of a triazine skeleton)).

The ratio of the peak area of the nitrogen-containing compound (B-2) to the polythiol compound (A-2) was determined in the following manner.

1. Measurement Conditions of High Performance Liquid Chromatography
   Column: YMC-Pack ODS-AA-312 (S5Φ6 mm×150 mm)
   Mobile phase: acetonitrile/0.01 mol-potassium dihydrogen phosphate aqueous solution=60/40 (vol/vol)
   Column temperature: 40° C.
   Flow rate: 1.0 ml/min
   Detector: UV detector, wavelength 230 nm
   Preparation of measurement solution: 160 mg of a sample is dissolved and mixed in 10 ml of acetonitrile.
   Injection volume: 2 µL 2. Ratio of Peak Area of Nitrogen-Containing Compound (B-2)

The composition ratio of the polythiol composition which was produced in Example C-1 was calculated using the following expression.

{[peak area of nitrogen-containing compound (B-2)]/
 [peak area of polythiol compound (A-2)]}×100    Expression The result calculated using the expression for computation described above was 1.16.

Figure 2:
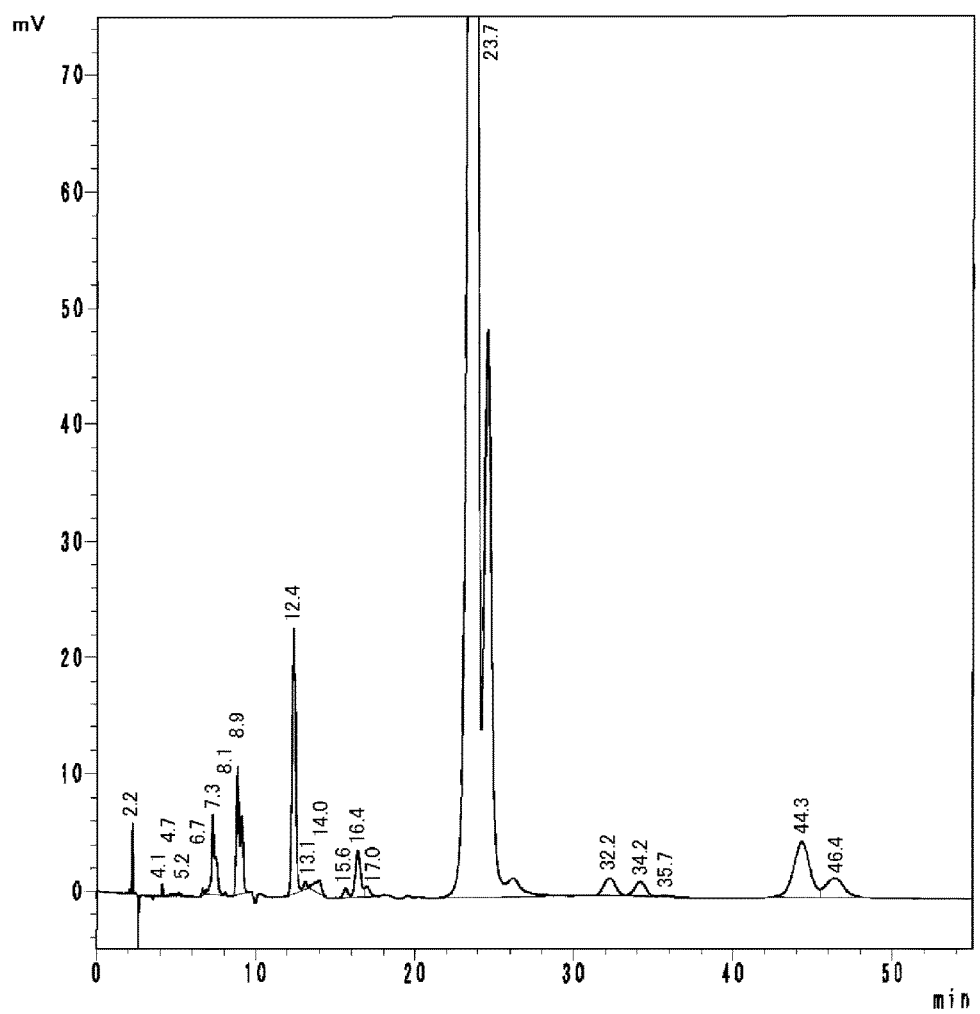
FIG. 2 shows a high performance liquid chromatography (HPLC) chart of a polythiol composition obtained in Example C-1.

Moreover, the retention times of the polythiol compound (A-2) and the nitrogen-containing compound (B-2) were as follows. A chart of high performance liquid chromatography is shown in FIG. 2.

Polythiol compound (A-2): From 22.0 minutes to 28.0 minutes Nitrogen-containing compound (B-2): From 6.5 minutes to 8.0 minutes (Manufacturing Plastic Lens)

50.7 parts by weight of m-xylylene diisocyanate, 0.01 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by KYODO CHEMICAL CO., LTD.; ultraviolet absorbing agent) were mixed and dissolved at 20° C. 49.3 parts by weight of the polythiol composition which is primarily comprised of the obtained polythiol compound (A-2) was charged and mixed to set to a mixed homogeneous liquid. After the homogeneous liquid was degassed at 600 Pa for 1 hour, the homogeneous liquid was put into a mold die consisting of a glass mold and a tape after filtrating using a Teflon (registered trademark) filter of 1 µm. The mold die was put into an oven, gradually heated up from 10° C. to 120° C., and polymerized for 20 hours. After the polymerization was finished, the mold die was taken out from the oven to obtain a resin by releasing from the mold die. The obtained resin was further annealed at 130° C. for 4 hours. Physical properties of the obtained lens are shown in Table-3.

Examples C-2 to C-10

The polythiol composition which is primarily comprised of the polythiol compound (A-2) in the same way as Example C-1 except setting to the producing conditions described in Table-3 was produced and the plastic lens was manufactured. The results are shown in Table-3.

Example D-1

Synthesis of Polythiol Composition which is Primarily comprised of bis(mercaptomethyl)-3,6,9-trithia-1,11-undecanedithiol 51.2 parts by weight of 2-mercaptoethanol, 26.5 parts by weight of degassed water (the concentration of dissolved oxygen is 2 ppm), and 0.16 parts by weight of 49% by weight sodium hydroxide aqueous solution were charged into a reaction vessel. 61.99 parts by weight of epichlorohydrin was added dropwise and charged from 9° C. to 13° C. over 6.5 hours, and continuously, stirring was performed for 40 minutes. From an NMR data, the production of 1-chloro-3-(2-hydroxyethylthio)-2-propanol was confirmed.

Next, 150.0 parts by weight of 17.3% sodium sulphide aqueous solution was added dropwise and charged from 5° C. to 42° C. over 4.5 hours, and continuously, stirring was performed for 40 minutes. From an NMR data, the production of a tetraol compound of the formula (4) was confirmed. Next 117.4 parts by weight of the purity of 99.90% of thiourea was charged, 84.3 parts by weight of the purity of 90.7% of hydrochloric acid gas was blown and stirred at 110° C. for 3 hours under reflux to convert into a thiuronium salt. After cooling to 45° C., 214.0 parts by weight of toluene was added and cooled to 26° C., 158.4 parts by weight of 25% by weight aqueous ammonia solution was charged from 26° C. to 46° C. over 25 minutes and matured from 54° C. to 62° C. for 1 hour, and a toluene solution of the polythiol composition which is primarily comprised of the polythiol compound (A-2) consisting of 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane was obtained. 59.4 parts by weight of 36% hydrochloric acid was added into the toluene solution and acid washing which was performed from 33° C. to 40° C. for 30 minutes was conducted twice. 118.7 parts by weight of degassed water (the concentration of dissolved oxygen is 2 ppm) was added and washing which was performed from 35° C. to 45° C. for 30 minutes was conducted five times. After toluene and trace water were removed under heating and reduced pressure, filtration under reduced pressure was performed by PTFE type membrane filter of 1.2 µm to obtain 115.0 parts by weight of the polythiol composition which is primarily comprised of the polythiol compound (A-2). Physical properties of the obtained polythiol composition are shown in Table-3. The identification of the polythiol compounds was performed by an NMR, and the same results as Example C-1 were obtained.

(Fractionation and Structure Confirmation)

The nitrogen-containing compound (referred to as B-2) included in the polythiol composition was fractionated from the polythiol composition which is primarily comprised of the polythiol compound (A-2) by performing preparative high performance liquid chromatography.

From the results of instrumental analysis, it was proved that the nitrogen-containing compound (B-2) had a structure in which one of a mercapto group of the polythiol compound (A-2) was replaced with a group represented by the following formula (a), furthermore, other one of a mercapto group was replaced with a hydroxyl group. In the following formula (a), * represents an atomic bonding.

The results of an analysis of the nitrogen-containing compound (B-2) included in the polythiol composition are shown.

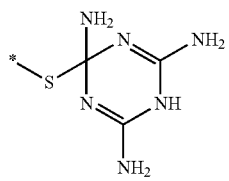

(a)

(1) Mass Spectrum
FAB-MS: m/z 476 (M$^+$) (Matrix m-NBA)
(2) IR (Universal ATR Method):
3329, 3198 cm$^{-1}$: NH stretching, 2539 cm$^{-1}$: SH stretching, 1606 cm$^{-1}$: C=N stretching, 1525 cm$^-$: NH vending.
(3) $^1$H-NMR (CDCl$_3$):
δ ppm 1.6-1.8 (4H(SH)), 2.5-3.5 (33H (—CH$_2$—, —CH—)), 3.8-3.9 (3H (—CHOH, CH$_2$OH)).
(4) $^{13}$C-NMR (CDCl$_3$):
δ ppm 25-39 (CH$_2$), 48-50 (CH), 61 (CH$_2$—OH(C adjacent to O)), 69-70 (CH—OH(C adjacent to O)), 166, 180 (—C—N—(C of a triazine skeleton)).

The ratio of the peak area of the nitrogen-containing compound (B-2) to the polythiol compound (A-2) was determined by performing in the same way as Example C-1.

(Manufacturing Plastic Lens)

50.7 parts by weight of m-xylylene diisocyanate, 0.01 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by KYODO CHEMICAL CO., LTD.; ultraviolet absorbing agent) were mixed and dissolved at 20° C. 49.3 parts by weight of the polythiol composition which is primarily comprised of the obtained polythiol compound (A-2) was charged and mixed to set to a mixed homogeneous liquid. After the homogeneous liquid was degassed at 600 Pa for 1 hour, the homogeneous liquid was put into a mold die consisting of a glass mold and a tape after filtrating using a Teflon (registered trademark) filter of 1 μm. The mold die was put into an oven, gradually heated up from 10° C. to 120° C., and polymerized for 20 hours. After the polymerization was finished, the mold die was taken out from the oven to obtain a resin by releasing from the mold die. The obtained resin was further annealed at 130° C. for 4 hours. Physical properties of the obtained lens are shown in Table-3.

Examples D-2 to D-10

The polythiol composition which is primarily comprised of the polythiol compound (A-2) in the same way as Example D-1 except setting to the producing conditions described in Table-3 was produced and the plastic lens was manufactured. The results are shown in Table-3.

TABLE 3

| | Condition I | Condition II | | Condition III | | Monomer analysis value | | | | | | | Ratio of peak area of nitrogen-containing compound | Evaluation of resin | | |
|---|---|---|---|---|---|---|---|---|---|---|---|---|---|---|---|---|
| | Diolated temperature ° C. | Charging temperature ° C. | Charging time Minute | Acid washing concentration % | Acid washing temperature ° C. | Color | Specific Gravity | Acidity ppm | Water ppm | Viscosity mPa·s | Refractive index | NH$_4$ ppm | | Color YI | loss degree of transparency % | Striation |
| Example C-1 | 9-11 | 26-50 | 30 | 36 | 34-39 | 15 | 1.290 | 24 | 80 | 212 | 1.6474 | 0.03 | 1.16 | 4.4 | 23 | ◯ |
| Example C-2 | 9-13 | 26-50 | 28 | 36 | 35-40 | 15 | 1.289 | 22 | 90 | 208 | 1.6473 | 0.03 | 1.08 | 4.4 | 21 | ◯ |
| Example C-3 | 9-12 | 26-50 | 28 | 36 | 35-40 | 15 | 1.290 | 27 | 40 | 210 | 1.6476 | 0.02 | 1.09 | 4.4 | 22 | ◯ |
| Example C-4 | 9-13 | 26-50 | 28 | 36 | 35-40 | 15 | 1.290 | 24 | 70 | 209 | 1.6476 | 0.04 | 1.11 | 4.4 | 22 | ◯ |
| Example C-5 | 9-12 | 26-50 | 28 | 36 | 35-40 | 15 | 1.290 | 25 | 50 | 208 | 1.6475 | 0.02 | 1.18 | 4.3 | 23 | ◯ |
| Example C-6 | 9-12 | 26-50 | 28 | 36 | 35-40 | 15 | 1.290 | 22 | 50 | 209 | 1.6474 | 0.04 | 1.18 | 4.4 | 21 | ◯ |
| Example C-7 | 9-12 | 26-50 | 28 | 36 | 35-40 | 15 | 1.290 | 23 | 80 | 208 | 1.6477 | 0.01 | 1.17 | 4.4 | 21 | ◯ |
| Example C-8 | 9-12 | 26-50 | 30 | 36 | 35-40 | 15 | 1.288 | 22 | 90 | 209 | 1.6474 | 0.03 | 1.15 | 4.4 | 21 | ◯ |
| Example C-9 | 9-12 | 26-50 | 28 | 30 | 35-39 | 15 | 1.290 | 26 | 60 | 214 | 1.6476 | 0.03 | 1.25 | 4.4 | 22 | ◯ |
| Example C-10 | 9-13 | 26-50 | 30 | 30 | 35-39 | 15 | 1.290 | 25 | 20 | 215 | 1.6475 | 0.03 | 1.30 | 4.5 | 23 | ◯ |
| Example D-1 | 9-13 | 26-46 | 25 | 36 | 33-40 | 10 | 1.290 | 12 | 20 | 206 | 1.6474 | 0.02 | 1.20 | 4.0 | 18 | ◯ |
| Example D-2 | 9-15 | 26-47 | 25 | 36 | 31-37 | 10 | 1.290 | 11 | 20 | 206 | 1.6474 | 0.03 | 0.97 | 4.0 | 18 | ◯ |
| Example D-3 | 9-13 | 26-47 | 25 | 36 | 31-37 | 10 | 1.290 | 14 | 40 | 208 | 1.6474 | 0.02 | 1.10 | 4.2 | 18 | ◯ |
| Example D-4 | 8-13 | 26-47 | 25 | 36 | 32-37 | 10 | 1.290 | 14 | 30 | 208 | 1.6474 | 0.04 | 1.17 | 4.2 | 17 | ◯ |
| Example D-5 | 9-14 | 26-47 | 25 | 36 | 32-37 | 10 | 1.290 | 12 | 40 | 208 | 1.6474 | 0.02 | 1.08 | 4.0 | 17 | ◯ |
| Example D-6 | 9-12 | 26-48 | 25 | 36 | 31-37 | 10 | 1.290 | 19 | 60 | 213 | 1.6474 | 0.03 | 1.45 | 4.2 | 18 | ◯ |

TABLE 3-continued

| | Condition I | Condition II | | Condition III | | Monomer analysis value | | | | | | | Ratio | Evaluation of resin | | |
| | Diolated temperature ° C. | Charging temperature ° C. | Charging time Minute | Acid washing concentration % | Acid washing temperature ° C. | Color | Specific Gravity | Acidity ppm | Water ppm | Viscosity mPa·s | Refractive index | NH$_4$ ppm | of peak area of nitrogen-containing compound | Color YI | loss degree of transparency % | Striation |
|---|---|---|---|---|---|---|---|---|---|---|---|---|---|---|---|---|
| Example D-7 | 9-14 | 26-49 | 25 | 36 | 31-37 | 10 | 1.290 | 19 | 40 | 215 | 1.6474 | 0.03 | 1.39 | 4.2 | 18 | ○ |
| Example D-8 | 9-13 | 26-47 | 25 | 36 | 33-37 | 10 | 1.290 | 17 | 50 | 213 | 1.6473 | 0.02 | 1.20 | 4.1 | 19 | ○ |
| Example D-9 | 5-15 | 26-47 | 25 | 30 | 32-36 | 10 | 1.290 | 14 | 60 | 208 | 1.6472 | 0.02 | 1.19 | 4.1 | 19 | ○ |
| Example D-10 | 9-13 | 26-48 | 25 | 30 | 32-39 | 10 | 1.290 | 14 | 20 | 208 | 1.6471 | 0.02 | 1.16 | 4.2 | 20 | ○ |

Condition I: Conditions of reacting 2-mercaptoethanol with epichlorohydrin.
Condition II: Conditions of charging an ammonia aqueous solution in a hydrolysis reaction.
Condition III: Conditions of hydrochloric acid washing.
Ratio of peak area of nitrogen-containing compound: Expression {[peak area of nitrogen-containing compound (B-2)]/[peak area of polythiol compound (A-2)]} × 100

Examples II-1 to 11-3, Comparative Example II-1

Preparation of Thiol Composition Added the Predetermined Amount of Nitrogen-Containing Compound (B-2)

The predetermined amount of the nitrogen-containing compound (B-2) which was fractionated in advance was added to the polythiol composition that is primarily comprised of the polythiol compound (A-2), the ratio of the peak area of the nitrogen-containing compound (B-2) was analyzed by high performance liquid chromatography in accordance with the conditions described above. The results are shown in Table-4.

(Viscosity Measurement of Polymerizable Composition)

The producing time of the polymerizable composition was set to 0 hour and the viscosity after 7 hours was evaluated as an index.

50.7 parts by weight of m-xylylene diisocyanate, 0.015 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by KYODO CHEMICAL CO., LTD.; ultraviolet absorbing agent) were mixed and dissolved at 20° C. 49.3 parts by weight of the polythiol composition which is primarily comprised of the obtained polythiol compound (A-2) was charged and mixed to set to a mixed homogeneous liquid. The producing time of the mixed homogeneous solution was set to 0 hour and the viscosity after 7 hours was evaluated by a Brookfield type viscometer. The results are shown in Table-4.

(Manufacturing Plastic Lens)

50.7 parts by weight of m-xylylene diisocyanate, 0.01 parts by weight of dibutyltin dichloride as a curing catalyst, 0.10 parts by weight of ZELEC UN (trade name, a product manufactured by Stepan Company; acidic phosphoric ester), 0.05 parts by weight of Viosorb 583 (trade name, manufactured by CHEMICAL CO., LTD.; ultraviolet absorbing agent) were mixed and dissolved at 20° C. 49.3 parts by weight of the polythiol composition which is primarily comprised of the obtained polythiol compound (A-2) was charged and mixed to set to a mixed homogeneous liquid. After the homogeneous liquid was degassed at 600 Pa for 1 hour, the homogeneous liquid was put into a mold die consisting of a glass mold and a tape after filtrating using a Teflon (registered trademark) filter of 1 μm. The mold die was put into an oven, gradually heated up from 10° C. to 120° C., and polymerized for 20 hours. After the polymerization was finished, the mold die was taken out from the oven to obtain a resin by releasing from the mold die. The obtained resin was further annealed at 130° C. for 4 hours. Physical properties of the obtained plastic lens are shown in Table-4.

TABLE 4

| | | Ratio of peak area of nitrogen-containing compound (B-2) | Viscosity after 7 hours (mPa·s) | Evaluation of resin | | |
| | | | | Color YI | Loss degree of transparency % | Striation |
|---|---|---|---|---|---|---|
| Example | II-1 | 0.75 | 175 | 4.1 | 23 | ○ |
| | II-2 | 1.50 | 209 | 4.1 | 22 | ○ |
| | II-3 | 2.80 | 569 | 4.3 | 30 | ○ |
| Comparative Example | II-1 | 3.20 | 1000< | 4.3 | 28 | X |

Ratio of peak area of nitrogen-containing compound
Expression: {[peak area of nitrogen-containing compound (B-2)]/[peak area of polythiol compound (A-2)]} × 100

From the results described above, in a case where the ratio of the peak area of the nitrogen-containing compound (B-2) to the polythiol compound (A-2) was 3.0 or less as Examples II-1 to 11-3, color and the loss degree of transparency were excellent and striation also did not occur. Furthermore, the viscosity of the polymerizable composition after 7 hours was low and handling characteristics were excellent.

On the other hand, in a case where the ratio of the peak area of the nitrogen-containing compound (B-2) was over 3.0 as Comparative Example II-1, since the viscosity of the polymerizable composition after 7 hours was over 1,000 mPa·s, it became clear that manufacturing stability of the plastic lens was also affected.

This application claims a priority based on Japanese Patent Application No. 2012-179899, filed Aug. 14, 2012 and a priority based on PCT/JP2013/001201, filed Feb. 28, 2013, and all disclosure of these references are incorporated in the present application.

The invention claimed is:

1. A polythiol composition comprising:
a polythiol compound (A) having three or more mercapto groups; and
a nitrogen-containing compound (B) in which one of a mercapto group of the polythiol compound (A) is replaced with a group represented by the following formula (a)

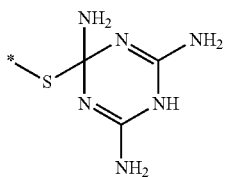

(a)

wherein, in the formula, * represents an atomic bonding, and other one of a mercapto group of the polythiol compound (A) is replaced with a hydroxyl group,
wherein the peak area of the nitrogen-containing compound (B) is equal to or less than 3.0, with respect to the peak area of 100 of the polythiol compound (A) in a high performance liquid chromatography measurement.

2. The polythiol composition according to claim 1, wherein the polythiol compound (A) is represented by the following formula (5)

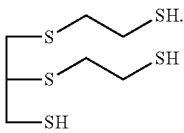

(5)

3. The polythiol composition according to claim 1, wherein the polythiol compound (A) is primarily comprised of at least one kind selected from the compounds represented by the following formulae (6) to (8)

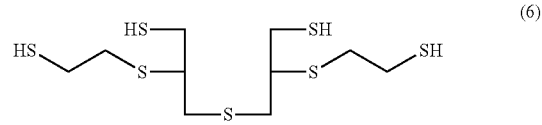

(6)

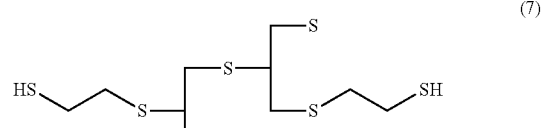

(7)

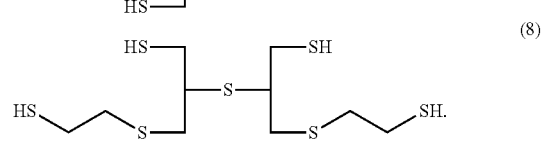

(8)

4. A polymerizable composition for an optical material comprising:
the polythiol composition according to claim 1; and
a poly(thio)isocyanate compound.

5. A method of manufacturing a molded product, comprising:
mixing the polythiol composition according to claim 1 and a poly(thio)isocyanate compound to obtain a polymerizable composition for an optical material; and
injecting the polymerizable composition into a mold and curing the composition.

6. A molded product which is obtained by curing the polymerizable composition according to claim 4.

7. An optical element comprised of the molded product according to claim 6.

8. A lens comprised of the optical element according to claim 7.

* * * * *